United States Patent
Kay et al.

(12)

(10) Patent No.: US 6,524,814 B1
(45) Date of Patent: *Feb. 25, 2003

(54) ENZYME AND DNA SEQUENCE ENCODING KRILL-DERIVED MULTIFUNCTIONAL PROTEIN

(75) Inventors: John Kay, Cardiff (GB); Peter Kille, Cardiff (GB)

(73) Assignee: Phairson Medical, Inc., London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/242,999

(22) PCT Filed: Aug. 28, 1997

(86) PCT No.: PCT/US97/15179

§ 371 (c)(1),
(2), (4) Date: Oct. 26, 1999

(87) PCT Pub. No.: WO98/08863

PCT Pub. Date: Mar. 5, 1998

(51) Int. Cl.[7] .......................... C12N 21/06; C12N 9/00; C12N 9/64; C07H 21/02; C07H 21/04
(52) U.S. Cl. .................. 435/69.1; 435/325; 435/320.1; 435/252.3; 435/455; 435/183; 435/219; 435/226; 536/23.1; 536/23.2; 536/23.5
(58) Field of Search .............................. 536/23.5, 23.1, 536/23.2; 435/320.1, 325, 69.1, 183, 455, 252.3, 219, 226; 530/350

(56) References Cited

U.S. PATENT DOCUMENTS 6,040,155 A * 5/2000 Kay et al. .................. 435/69.1

FOREIGN PATENT DOCUMENTS

WO   WO 9533479    12/1995
WO   WO 96/24371    8/1996

OTHER PUBLICATIONS

Anheller et al, Arch Dermatol Res 281:105–110, 1989.*
Anderson WF, Nature 392:25–30, 1998.*
Verma et al Nature 389:239–242, 1997.*
Kay et al, PNAS 94:12744–12746, 1997.*
Anheller, et. al., "Biochemical and Biological Profile of a New Enzyme Preparation from Antartic Krill (*E. Superba*) suitable for Debridement of Ulcerative Lesions." Arch Dermatological Research vol. 281, pp. 105–110, (1989).

* cited by examiner

*Primary Examiner*—Scott D. Priebe
*Assistant Examiner*—Sumesh Kaushal
(74) *Attorney, Agent, or Firm*—Dechert

(57) ABSTRACT

The present invention provides nucleic acid and corresponding amino acid sequences of a multifunctional protein that has been found to be useful in numerous medical and cosmetic contexts. A protein having "multifunctional activity," is defined herein as including at least one of a chymotrypsin, trypsin, collagenase, elastase or exo peptidase activity or asialo $GM_1$ ceramide binding activity. These proteins are useful for multiple purposes, including treating viral infections such as herpes outbreaks, fungal, bacterial or parasitic infections, including the primary and secondary infections of leprosy, colitis, ulcers, hemorrhoids, corneal scarring, dental plaque, acne, cystic fibrosis, blood clots, wounds, immune disorders including autoimmune disease and cancer.

6 Claims, 10 Drawing Sheets

Nucleotide alignment of p62 with p31

88.0% identity in 590 bp overlap

```
              320       330       340       350       360       370
p62    TATGGATGGTGCTGGGTTTGTTGAGGTTGTGATGGGTGCTCACAGTATCCATGACGAAAC
                                    ||||||||||||||||||||||||||| ||
p31                                 GATGGGTGCTCACAGTATCCATGACGATAC
                                             10        20        30

380       390       400       410       420       430
p62    TGAGGCCACACAGGTCCGTGCCACATCAACTGATTTCTTCACCCACGAGAACTGGAACTC
       ||||||| | |   ||| ||||||||||||||||||||||||||||||||||||||||||
p31    TGAGGCCTCTCGCGTCAGTGCCACATCAACTGATTTCTTCACCCACGAGAACTGGAACTC
               40        50        60        70        80        90

440       450       460       470       480       490
p62    CTTCACCCTCTCCAATGATCTTGCTCTCATTAAGATGCCAGCACCAATTGAATTCAACGA
       |||||||||| |||||||||||||||||||||||||||||||||||||||||||||| 
p31    CTTCACCCTCACCAATGATCTTGCTCTCATTAAGATGCCAGCACCAATTGAATTCACACC
              100       110       120       130       140       150

500       510       520       530       540       550
p62    TGTGATCCAGCCTGTCTGCCTACCAACCTATACTGATGCTAGTGATGATTTTGTTGGTGA
       ||  || || |||||||||||||||| ||| ||||||||||  |||||||| |||||||
p31    TGAAATTCAACCTGTCTGCCTACCAAGCTACACTGATGCTGCTGATGATTTCATTGGTGA
              160       170       180       190       200       210

560       570       580       590       600       610
p62    ATCAGTCACTCTTACTGGATGGGGTAAACCATCTGACTCTGCTTTTGGCATCGCTGAACA
       ||| ||   ||||||||||||||||  |||| | ||||||  ||||||| ||| |||| 
p31    ATCTGTTGTCCTTACTGGATGGGGCCGTGATTCTGATGCTGCTTCCGGCATCTCTGAACT
              220       230       240       250       260       270

620       630       640       650       660       670
p62    ACTTCGTGAGGTTGATGTGACAACAATCACTACTGCTGACTGCCAGGCATACTACGGCAT
       || | |||||||| ||||||||| |||||  |||| |||| |||||||||||||||||
p31    ACTCCGTGAGGTTCATGTGACCACAATCTCCACTGCCGACTGCCAGGCATACTACGGCAT
              280       290       300       310       320       330

680       690       700       710       720       730
p62    TGTCACTGACAAAATCCTCTGCATCGACTCCGAAGGAGGCCATGGTTCCTGCAATGGTGA
       |||||||||||||||||||||||| |  ||| || ||||||||||||| || ||||||||
p31    TGTCACTGACAAAATCCTCTGCATTTCCTCTGAAGACGGACATGGTTCTTGTAATGGTGA
              340       350       360       370       380       390

740       750       760       770       780       790
p62    TTCCGGCGGGCCAATGAACTATGTAACTGGTGGTGTTACTCAGACCCGTGGTATTACCTC
       ||||||| |||||||||||||||||||||||||||||||||||||||||||||||||||
p31    TTCCGGTGGGCCAATGAACTATGTAACTGGTGGTGTTACTCAGACCCGTGGTATTACCTC
              400       410       420       430       440       450

800       810       820       830       840       850
p62    TTTCGGATCCTCTACCGGCTGCGAGACTGGCTACCCTGATGGTTACACACGAGTCACCAG
       |||||||||||||||||| || ||||||||||||||||||||||||||||| ||||||
p31    CTTCGGATCCTCTACCGGGTGTGAGACTGGCTACCCTGATGGTTACACACGTGTCACCAG
              460       470       480       490       500       510
```

Figure 1

```
            860       870       880       890       900       910
p62  CTATCTGGACTGGATTGAATCTAACACTGGCATTGCCATTGATCCATAAATACAATTCTA
     ||||||||||||||||||||||||||||||||||||||||||||| | |||| ||| |||
p31  CTATCTGGACTGGATTGAATCTAACACTGGCATTGCCATTGATGCTTGAATATAATACTA
            520       530       540       550       560       570

920       930       940
p62  GCAA--AAATACAATAAATTATACTTAAATG
     |  |   |||  ||||||||
p31  GATATGTAATCAAATAAATTTCATGAATT
            580       590
```

Figure 1A

Protein Alignment of p62 and 31

−89% identity in 189 amino acid overlap

```
p62                                    LLLALVAAASAAEWRWQFRHPTVTP p62  NPRAKNPFRVTKSSPVQPPAVRGTKAVENCGPVAPRNKIVGGMEVTPHAYPWQVGLFIDD p62  MYFCGGSIISDEWVLTAAHCMDGAGFVEVVMGAHSIHDETEATQVRATSTDFFTHENWNS
                                  ||||||||:|||::|:|||||||||||||
p31                               MGAHSIHDDTEASRVSATSTDFFTHENWNS p62  FTLSNDLALIKMPAPIEFNDVIQPVCLPTYTDASDDFVGESVTLTGWGKPSDSAFGIAEQ
     |||:||||||||||||||:  |||||||:||||:|||:||||:|||||:  ||:| ||:|
p31  FTLTNDLALIKMPAPIEFTPEIQPVCLPSYTDAADDFIGESVVLTGWGRDSDAASGISEL p62  LREVDVTTITTADCQAYYGIVTDKILCIDSEGGHGSCNGDSGGPMNYVTGGVTQTRGITS
     ||||:||||:|||||||||||||||||||:||:|||||||||||||||||||||||||||
p31  LREVHVTTISTADCQAYYGIVTDKILCISSEDGHGSCNGDSGGPMNYVTGGVTQTRGITS p62  FGSSTGCETGYPDGYTRVTSYLDWIESNTGIAIDP
     ||||||||||||||||||||||||||||||||||:
p31  FGSSTGCETGYPDGYTRVTSYLDWIESNTGIAIDA
```

Figure 2

```
SCORES                   Initl: 1584  Initn: 1657  Opt: 1653
                    89.1% identity in 514 bp overlap 10        20        30        40        50        60
p5.1   CCCGGGCAGGTCCAGGATCGCCCTCTTACTTGCCCTTGTGGCTGCTACAGCTAGTGCTTC
                              ||||||||| ||||||||||||||||||  ||||||| |
P62                           CTCTTACTCGCCCTTGTGGCTGCT---GCTAGTGCCGC
                                 10        20           30

70        80        90       100       110       120
p5.1   AGAATGGCGCTGGCAGTTCCGTCACCCCACTGTGACCCCCAACCCCAGAGCTAACAACCC
       |||||||||||||||||| ||||||||| ||| |||||||||||||| || ||||| ||||
P62    AGAATGGCGCTGGCAGTTTCGTCACCCTACAGTGACCCCCAACCCTAGGGCTAAGAACCC
           40        50        60        70        80        90

130       140       150       160       170       180
p5.1   CTTCAGACCCAGTAAAGTCGCTCCAGTCCAACCACCAGCAGTCAGAGGAACAAAGGCTGT
       ||||||| || ||| | ||||||||||||||||||||||||||||||||||||||||||||
p62    CTTCAGAGTCACCAAAAGCTCTCCAGTCCAACCACCAGCAGTCAGAGGAACAAAGGCTGT
          100       110       120       130       140       150

190       200       210       220       230       240
p5.1   TGAGAACTGTGGACCAGTAGCACCAAAGAACAAGATTGTAGGAGGGCAAGAAGTGACTCC
       |||||||||||||||||||||||||||| |||||||||||||||||  || |||||||||
p62    TGAGAACTGTGGACCAGTAGCACCAAGGAACAAGATTGTAGGAGGCATGGAGGTGACTCC
          160       170       180       190       200       210

250       260       270       280       290       300
p5.1   CCATGCTTACCCCTGGCAGGTGGGACTCTTCATCGATGACATGTACTTCTGCGGTGGATC
       |||||||||||||||||||||||||||| |||| ||||| ||||||||||| ||||||||
p62    CCATGCTTACCCCTGGCAGGTGGGACTTTTCATTGATGATATGTACTTCTGTGGTGGATC
          220       230       240       250       260       270

310       320       330       340       350       360
p5.1   CATCATCTCAGAGGACTGGGTGCTTACAGCTGCTCACTGTGTGGATGGTGCTGGTTTTGT
       |||||||| || || |||||| ||||||||||||||||||| |||||||||||| |||||
p62    AATCATCTCCGACGAATGGGTCCTTACAGCTGCTCACTGTATGGATGGTGCTGGGTTTGT
          280       290       300       310       320       330

370       380       390       400       410       420
p5.1   CGAAGTTGTGATGGGTGCTCACAGTATCCATGACGATACTGAGGCCTCTCGCATCAGTGC
       || |||||||||||||||||||||||||||||||||| ||||||||| | ||  || ||||
p62    TGAGGTTGTGATGGGTGCTCACAGTATCCATGACGAAACTGAGGCCACACAGGTCCGTGC
          340       350       360       370       380       390

430       440       450       460       470       480
p5.1   CACATCAACTGATTTCTTCACCCACGAGAACTGGAACTCCTTCACCCTCACCAATGATCT
       |||||||||||||||||||||||||||||||||||||||||||||||||| ||||||||||
p62    CACATCAACTGATTTCTTCACCCACGAGAACTGGAACTCCTTCACCCTCTCCAATGATCT
          400       410       420       430       440       450

490       500       510       520       530
p5.1   TGCTCTCATTAAGATGCCAGCACCCATTGAGTTCACACCTGAAATTCAACCTGTCT
       |||||||||||||||||||||||||||| |||| ||||   || || || ||||||||
p62    TGCTCTCATTAAGATGCCAGCACCAATTGAATTCAACGATGTGATCCAGCCTGTCTGCCT
          460       470       480       490       500       510 p62    ACCAACCTATACTGATGCTAGTGATGATTTTGTTGGTGAATCAGTCACTCTTACTGGATG
          520       530       540       550       560       570
```

Figure 3

```
       1                                                               50
p5.1   PGRSRIALLL ALVAATASAS EWRWQFRHPT VTPNPRANNP FRPSKVAPVQ
p62    .......LLL ALVAA.ASAA EWRWQFRHPT VTPNPRAKNP FRVTKSSPVQ
p31    .......... .......... .......... .......... ..........

51                                                              100
p5.1   PPAVRGTKAV ENCGPVAPKN KIVGGQEVTP HAYPWQVGLF IDDMYFCGGS
p62    PPAVRGTKAV ENCGPVAPRN KIVGGMEVTP HAYPWQVGLF IDDMYFCGGS
p31    .......... .......... .......... .......... ..........

101                                                             150
p5.1   IISEDWVLTA AHCVDGAGFV EVVMGAHSIH D TEA   I A TSTDFFTHEN
p62    IISDEWVLTA AHCMDGAGFV EVVMGAHSIH DETEATQVRA TSTDFFTHEN
p31    .......... .......... ...MGAHSIH D TEA   V A TSTDFFTHEN 151                                                             200
p5.1   WNSFTL NDL ALIKMPAPIE F    IQPV.. .......... ..........
p62    WNSFTLSNDL ALIKMPAPIE FNDVIQPVCL PTYTDASDDF VGESVTLTGW
p31    WNSFTL NDL ALIKMPAPIE F    IQPVCL PSYTDAADDF IGESVVLTGW 201                                                             250
p5.1   .......... .......... .......... .......... ..........
p62    GKPSDSAFGI AEQLREVDVT TITTADCQAY YGIVTDKILC IDSEGGHGSC
p31    GRDSDAASGI SELLREVHVT TISTADCQAY YGIVTDKILC ISSEDGHGSC 251                                                             300
p5.1   .......... .......... .......... .......... ..........
p62    NGDSGGPMNY VTGGVTQTRG ITSFGSSTGC ETGYPDGYTR VTSYLDWIES
p31    NGDSGGPMNY VTGGVTQTRG ITSFGSSTGC ETGYPDGYTR VTSYLDWIES 301         322
p5.1   .......... .......... ..
p62    NTGIAIDP.. .......... ..
p31    NTGIAIDA
```

Figure 4

```
62:                         CTCTTACTCGCCCTTGTGGCTGCT    GCTAGTGCCGCA
912:               ATCGCCCTCTTACTCGCCCTTGTGGCTGCCACTGCTAGTGCTTCA
5.1b:      CCCGGGCAGGTCCAGGATCGCCCTCTTACTTGCCCTTGTGGCTGCTACAGCTAGTGCTTCA
AA/62:                      LeuLeuLeuAlaLeuValAlaAla    AlaSerAlaAla
AA/912:            IleAla------------------------Thr--------Ser
AA/5.1b:   ProGlyArgSerArgIleAla------------------------Thr--------Ser

62:        GAATGGCGCTGGCAGTTTCGTCACCCTACAGTGACCCCCAACCCTAGGGCTAAGAACCCC
912:       GAATGGCGCTGGCAGTTCCGTCACCCCACCGTGACCCCCAACCCCAGAGCTAACAACCCC
5.1b:      GAATGGCGCTGGCAGTTCCGTCACCCCACTGTGACCCCCAACCCCAGAGCTAACAACCCC
AA/62:     GluTrpArgTrpGlnPheArgHisProThrValThrProAsnProArgAlaLysAsnPro
AA/912:    ------------------------------------------------Asn------
AA/5.1b:   ------------------------------------------------Asn------

62:        TTCAGAGTCACCAAAAGCTCTCCAGTCCAACCACCAGCAGTCAGAGGAACAAAGGCTGTT
912:       TTCAGACCAAGTAAAGTTGCTCCAGTCCAACCACCAGCAGTCAGAGGAACAAAGGcTGTA
5.1b:      TTCAGACCCAGTAAAGTCGCTCCAGTCCAACCACCAGCAGTCAGAGGAACAAAGGCTGTT
AA/62:     PheArgValThrLysSerSerProValGlnProProAlaValArgGlyThrLysAlaVal
AA/912:    ------ProSer---ValAla-----------------------------------
AA/5.1b:   ------ProSer---ValAla-----------------------------------

62:        GAGAACTGTGGACCAGTAGCACCAAGGAACAAGATTGTAGGAGGCATGGAGGTGACTCCC
912:       CCCAACTGTGGACAGTCAAAGTCT    ACCAAGATTGTAGGAGGTGGTGAGGTAACTCCC
5.1b:      GAGAACTGTGGACCAGTAGCACCAAAGAACAAGATTGTAGGAGGGCAAGAAGTGACTCCC
AA/62:     GluAsnCysGlyProValAlaProArgAsnLysIleValGlyGlyMetGluValThrPro
AA/912:    Pro---------GlnSerLysSer   Thr---------------Gly-----------
AA/5.1b:   --------------------Lys------------------Gln-----------

62:        CATGCTTACCCCTGGCAGGTGGGACTTTTCATTGATGATATGTACTTCTGTGGTGGATCA
13:        CACGCCTACCCGTGGCAGGTGGGACTTTTCATTGATGATATGTACTTCTGTGGAGGATCA
912:       CATGCTTACCCCTGGCAGGtGGGACTTTTCATTGATGACATGTACTTCTGCGGKGGATCC
5.1b:      CATGCTTACCCCTGGCAGGTGGGACTCTTCATCGATGACATGTACTTCTGCGGTGGATCC
AA/62:     HisAlaTyrProTrpGlnValGlyLeuPheIleAspAspMetTyrPheCysGlyGlySer
AA/13:     ------------------------------------------------------------
AA/912:    ------------------------------------------------------------
AA/5.1b:   ---------------------------------------------------Phe---------

62:        ATCATCTCCGACGAATGGGTCCTTACAGCTGCTCACTGTATGGATGGTGCTGGGTTTGTT
13:        ATCATCTCCGACGAATGGGTCCTTACAGCTGCTCACTGTATGGATGGTGCTGGATTTGTT
912:       ATCATCTCAGAGGACTGGGTCCTTACAGCTGCTCACTGTATGGATGGTGCTGGGTTTGTT
5.1b:      ATCATCTCAGAGGACTGGGTCGTTACAGCTGCTCACTGTGTGGATGGTGCTGGTTTTGTC
AA/62:     IleIleSerAspGluTrpValLeuThrAlaAlaHisCysMetAspGlyAlaGlyPheVal
  212
AA/13:     ------------------------------------------------------------
AA/912:    ---------GluAsp---------------------------------------------
AA/5.1b:   ---------GluAsp------Val------Arg--------------Arg---------
```

Figure 5 - Part 1

```
62:     GAGGTTGTGATGGGTGCTCACAGTATCCATGACGAAACTGAGGCCACACAGGTCCGTGCC
13:     GAGGTTGTGATGGGTGCTCACAGTATCCATGACGAAACTGAGGCCACACAGGTCCGTGCC
912:    GAGGTTGTGATGGGTGCTCACAAGATCCATGATGATACTGAGGCCTCTCGCGTCAGTGCC
5.1b:   GAAGTTGTGATGGGTGCTCACAGTATCCATGACGATACTGAGGCCTCTCGCATCAGTGCC
31:           GATGGGTGCTCACAGTATCCATGACGATACTGAGGCCTCTCGCGTCAGTGCC
AA/62:  GluValValMetGlyAlaHisSerIleHisAspGluThrGluAlaThrGlnValArgAla
AA/13:  ------------------------------------------------------------
AA/912: ----------------------Lys---------Asp---------SerArg---Ser---
AA/5.1b:----------------------------Leu---Asp---------SerArgMetSer---
AA/31:  ------------------------------Asp---------SerArg---Ser---
```

```
62:     ACATCAACTGATTTCTTCACCCACGAGAACTGGAACTCCTTCACCCTCTCCAATGATCTT
13:     ACATCAACTGATTTCTTCACACACGAGAACTGGAACTCCTTCACCCTCTCCAATGATCTT
912:    ATATCAACTGATTTCTTCACCCACGAGAACTGGAACTCCTTCCTTCTCACCAATGATCTT
5.1b    ACATCAACTGATTTCTTCACCCACGAGAACTGGAACTCCTTCACCCTCACCAATGATCTT
31      ACATCAACTGATTTCTTCACCCACGAGAACTGGAACTCCTTCACCCTCACCAATGATCTT
AA/62:  ThrSerThrAspPhePheThrHisGluAsnTrpAsnSerPheThrLeuSerAsnAspLeu
AA/13:  ------------------------------------------------------------
AA/912: Ile---------------------------------Leu---Thr---------
AA/5.1b:--------------------------------------------Thr---------
AA/31:  --------------------------------------------Thr---------
```

```
62:     GCTCTCATTAAGATGCCAGCACCAATTGAATTCAACGATGTGATCCAGCCTGTCTGCCTA
13:     GCTCTCATTAAGATGCCAGCACCAATTGAATTCAACGATGTGATCCAGCCTGTCTGCCTA
912:    GCTCTCATTAAGATGCCAGCACCCATTGCATTCACTGATGAGATCCAGCCTGTATGCCTG
5.1b    GCTCTCATTAAGATGCCAGCACCCATTGAGTTCACACCTGAAATTCAACCTGTCT
31:     GCTCTCATTAAGATGCCAGCACCAATTGAATTCACACCTGAAATTCAACCTGTCTGCCTA
AA/62:  AlaLeuIleLysMetProAlaProIleGluPheAsnAspValIleGlnProValCysLeu
AA/13:  ------------------------------------------------------------
AA/912: ------------------------Ala---Thr---Glu------------------
AA/5.1b:-------------------------ThrProGlu-----------
AA/31:  -------------------------ThrProGlu------------------
```

```
62:     CCAACCTATACTGATGCTAGTGATGATTTTGTTGGTGAATCAGTCACTCTTACTGGATGG
13:     CCAACCTATACTGATGCCAGTGATGATTTTGTTGGTGAATCAGTCACTCTTACTGGATGG
912:    CCAACCTACACTGACTCCGATGATGATTTTGTTGGTGAATCAGTCACTCTTACTGGCTGG
31:     CCAAGCTACACTGATGCTGCTGATGATTTCATTGGTGAATCTGTTTGTCCTTACTGGATGG
AA/62:  ProThrTyrThrAspAlaSerAspAspPheValGlyGluSerValThrLeuThrGlyTrp
AA/13:  ------------------------------------------------------------
AA/912: ------------SerAsp-----------------------------------
AA/31:  ---Ser-----------Ala---------Ile-----------Val------------
```

```
62:     GGTAAACCATCTGACTCTGCTTTTGGCATCGCTGAACAACTTCGTGAGGTTGATGTGACA
13:     GGTAAACCATCTGACTCTGCTTTTGGCATCGCTGAACAACTTCGTGAGGTTGATGTGACA
912:    GGTCGTGCATCTGACTCTGCTAGCGGCATCTCTGAAGTACTTCGTGAGGTTGATGTGACA
31:     GGCCGTGATTCTGATGCTGCTTCCGGCATCTCTGAACTACTCCGTGAGGTTCATGTGACC
AA/62:  GlyLysProSerAspSerAlaPheGlyIleAlaGluGlnLeuArgGluValAspValThr
212
AA/13:  ------------------------------------------------------------
AA/912: ---ArgAla------------Ser------Ser---Val----------------------
AA/31:  ---ArgAsp------Ala---Ser------Ser---Leu-----------His------
```

Figure 5 - Part 2

```
62:     Acaatcactactgctgactgccaggcatactacggcattgtcactgacaaaatcctctgc
13:     ACaatcactactgctgactgccaggcatactacggcattgtcactgacaaaatcctctgc
912:    ACAATAACTACTGCCGACTGCCAGGCATACTATGGTATTGTCACTGACAAAATCCTCTGC
31:     ACAATCTCCACTGCCGACTGCCAGGCATACTACGGCATTGTCACTGACAAAATCCTCTGC
AA/62:  ThrIleThrThrAlaAspCysGlnAlaTyrTyrGlyIleValThrAspLysIleLeuCys
        232
AA/13:  ------------------------------------------------------------
AA/912: ------------------------------------------------------------
AA/31   -----Ser----------------------------------------------------

62:     atcgactccgaaggaggccatggttcctgcaatggtgattccggCgggccaatgaactat
13:     atcgactccgaaggaggccatggttcctgcaatggtgattccggtgggccaatgaactat
912:    ATCGACTCAGAAGGAGGTCATGGGTCTTGCAATGGTGATTCCGGTGGGCCAATGAACTAT
31:     ATTTCCTCTGAAGACGGACATGGTTCTTGTAATGGTGATTCCGGTGGGCCAATGAACTAT
AA/62:  IleAspSerGluGlyGlyHisGlySerCysAsnGlyAspSerGlyGlyProMetAsnTyr
        252
AA/13:  ------------------------------------------------------------
AA/912: ------------------------------------------------------------
AA/31:  ---Ser------Asp---------------------------------------------

62:     gtaactggtggtgttactcagacccgtggtattacctctttcggatcctctaccggctgc
13:     gtaactggtggtgttactcagacccgtggtattacctctttcggatcctctaccggctgc
912:    GTAACTGGTGGTGTTACTCAGACCCGTGGTATTACCtcCTTCGGATCCTCTACCGGCTGT
31:     GTAACTGGTGGTGTTACTCAGACCCGTGGTATTACCTCCTTCGGATCCTCTACCGGGTGT
AA/62:  ValThrGlyGlyValThrGlnThrArgGlyIleThrSerPheGlySerSerThrGlyCys
        272
AA/13:  ------------------------------------------------------------
AA/912: ------------------------------------------------------------
AA/31:  ------------------------------------------------------------

62:     gagactggCtaccctgatGGttacacacgagtcACCAGCTATCTGGACTGGATTGAATCT
13:     gagactgggtaccctgataattacacacgagtc
912:    GAGACTGGCTACCCTGATGGTTACACACGAGTCACCAGCTATCTAGACTGGATTGAATCT
31:     GAGACTGGCTACCCTGATGGTTACACACGTGTCACCAGCTATCTGGACTGGATTGAATCT
AA/62:  GluThrGlyTyrProAspGlyTyrThrArgValThrSerTyrLeuAspTrpIleGluSer
        292
AA/13:  ------------------Asn---------------
AA/912: ------------------------------------------------------------
AA/31:  ------------------------------------------------------------

62:     AACACTGGCATTGCCATTGATCCATAAATACAATTCTAGCAAAAATACAATAAATTATAC
912:    AACACTGGCATTGCCATTGATCCTTGAATAATATTCTAGCTGAATGATAATAAATTCATG
31:     AACACTGGCATTGCCATTGATGCTTGAATATAATACTAGATATGTAATCAAATAAATTTC
AA/62:  AsnThrGlyIleAlaIleAspPro*
AA/912  -----------------------*
AA/31:  --------------------Ala*

62:     TTAAATG
912:    ATTGATAATCAAAAAAAAAAAAAAA
31:     ATGAATT
```

Figure 5 - Part 3

```
62:                         L   L   L   A   L   V   A   A       A   S   A   A    12
912:            I   A   L   L   L   A   L   V   A   A   T   A   S   A   S        15
5.1b:   P   G   R   S   R   I   A   L   L   L   A   L   V   A   A   T   A   S   A   S    20

62:     E   W   R   W   Q   F   R   H   P   T   V   T   P   N   P   R   A   K   N   P    32
912:    E   W   R   W   Q   F   R   H   P   T   V   T   P   N   P   R   A   N   N   P    35
5.1b:   E   W   R   W   Q   F   R   H   P   T   V   T   P   N   P   R   A   N   N   P    40

62:     F   R   V   T   K   S   S   P   V   Q   P   P   A   V   R   G   T   K   A   V    52
912:    F   R   P   S   K   V   A   P   V   Q   P   P   A   V   R   G   T   K   A   V    55
5.1b:   F   R   P   S   K   V   A   P   V   Q   P   P   A   V   R   G   T   K   A   V    60

62:     E   N   C   G   P   V   A   P   R   N   K   I   V   G   G   M   E   V   T   P    72
912:    P   N   C   G   Q   S   K   S       T   K   I   V   G   G   G   E   V   T   P    74
5.1b:   E   N   C   G   P   V   A   P   K   N   K   I   V   G   G   Q   E   V   T   P    80

62:     H   A   Y   P   W   Q   V   G   L   F   I   D   D   M   Y   F   C   G   G   S    92
13:     H   A   Y   P   W   Q   V   G   L   F   I   D   D   M   Y   F   C   G   G   S    20
912:    H   A   Y   P   W   Q   V   G   L   F   I   D   D   M   Y   F   C   G   G   S    94
5.1b:   H   A   Y   P   W   Q   V   G   L   F   I   D   D   M   Y   F   F   G   G   S   100

62:     I   I   S   D   E   W   V   L   T   A   A   H   C   M   D   G   A   G   F   V   112
13:     I   I   S   D   E   W   V   L   T   A   A   H   C   M   D   G   A   G   F   V    40
912:    I   I   S   E   D   W   V   L   T   A   A   H   C   M   D   G   A   G   F   V   114
5.1b:   I   I   S   E   D   W   V   V   T   A   R   H   C   M   D   G   R   G   F   V   120

62:     E   V   V   M   G   A   H   S   I   H   D   E   T   E   A   T   Q   V   R   A   132
13:     E   V   V   M   G   A   H   S   I   H   D   E   T   E   A   T   Q   V   R   A    60
912:    E   V   V   M   G   A   H   K   I   H   D   D   T   E   A   S   R   V   S   A   134
5.1b:   E   V   V   M   G   A   H   S   I   L   D   D   T   E   A   S   R   M   S   A   140
31:                     M   G   A   H   S   I   H   D   D   T   E   A   S   R   V   S   A    17

62:     T   S   T   D   F   F   T   H   E   N   W   N   S   F   T   L   S   N   D   L   152
13:     T   S   T   D   F   F   T   H   E   N   W   N   S   F   T   L   S   N   D   L    80
912:    I   S   T   D   F   F   T   H   E   N   W   N   S   F   L   L   T   N   D   L   154
5.1b:   T   S   T   D   F   F   T   H   E   N   W   N   S   F   T   L   T   N   D   L   160
31:     T   S   T   D   F   F   T   H   E   N   W   N   S   F   T   L   T   N   D   L    37

62:     A   L   I   K   M   P   A   P   I   E   F   N   D   V   I   Q   P   V   C   L   172
13:     A   L   I   K   M   P   A   P   I   E   F   N   D   V   I   Q   P   V   C   L   100
912:    A   L   I   K   M   P   A   P   I   A   F   T   D   E   I   Q   P   V   C   L   174
5.1b:   A   L   I   K   M   P   A   P   I   E   F   T   P   E   I   Q   P   V           180
31:     A   L   I   K   M   P   A   P   I   E   F   T   P   E   I   Q   P   V   C   L    57

62:     P   T   Y   T   D   A   S   D   D   F   V   G   E   S   V   T   L   T   G   W   192
13:     P   T   Y   T   D   A   S   D   D   F   V   G   E   S   V   T   L   T   G   W   120
912:    P   T   Y   T   D   S   D   D   D   F   V   G   E   S   V   T   L   T   G   W   194
31:     P   S   Y   T   D   A   A   D   D   F   I   G   E   S   V   V   L   T   G   W    77

62:     G   K   P   S   D   S   A   F   G   I   A   E   Q   L   R   E   V   D   V   T   212
13:     G   K   P   S   D   S   A   F   G   I   A   E   Q   L   R   E   V   D   V   T   140
912:    G   R   A   S   D   S   A   S   G   I   S   E   V   L   R   E   V   D   V   T   214
31:     G   R   D   S   D   A   A   S   G   I   S   E   L   L   R   E   V   H   V   T    97
```

Figure 6 - Part 1

```
62:    T  I  T  T  A  D  C  Q  A  Y  Y  G  I  V  T  D  K  I  L  C    232
13:    T  I  T  T  A  D  C  Q  A  Y  Y  G  I  V  T  D  K  I  L  C    160
912:   T  I  T  T  A  D  C  Q  A  Y  Y  G  I  V  T  D  K  I  L  C    234
31:    T  I  S  T  A  D  C  Q  A  Y  Y  G  I  V  T  D  K  I  L  C    117

62:    I  D  S  E  G  G  H  G  S  C  N  G  D  S  G  G  P  M  N  Y    252
13:    I  D  S  E  G  G  H  G  S  C  N  G  D  S  G  G  P  M  N  Y    180
912:   I  D  S  E  G  G  H  G  S  C  N  G  D  S  G  G  P  M  N  Y    254
31:    I  S  S  E  D  G  H  G  S  C  N  G  D  S  G  G  P  M  N  Y    137

62:    V  T  G  G  V  T  Q  T  R  G  I  T  S  F  G  S  S  T  G  C    272
13:    V  T  G  G  V  T  Q  T  R  G  I  T  S  F  G  S  S  T  G  C    200
912:   V  T  G  G  V  T  Q  T  R  G  I  T  S  F  G  S  S  T  G  C    274
31:    V  T  G  G  V  T  Q  T  R  G  I  T  S  F  G  S  S  T  G  C    157

62:    E  T  G  Y  P  D  G  Y  T  R  V  T  S  Y  L  D  W  I  E  S    292
13:    E  T  G  Y  P  D  N  Y  T  R  V                                211
912:   E  T  G  Y  P  D  G  Y  T  R  V  T  S  Y  L  D  W  I  E  S    294
31:    E  T  G  Y  P  D  G  Y  T  R  V  T  S  Y  L  D  W  I  E  S    177

62:    N  T  G  I  A  I  D  P                                         300
912:   N  T  G  I  A  I  D  P                                         302
31:    N  T  G  I  A  I  D  A  *                                      185
```

Figure 6 - Part 2

```
            1                                                          50
phim_p62    .......LLL ALVAA.ASAA EWRWQFRHPT VTPNPRAKNP FRVTKSSPVQ
phim_p912   .....IALLL ALVAATASAS EWRWQFRHPT VTPNPRANNP FRPSKVAPVQ
phim5_1     PGRSRIALLL ALVAATASAS EWRWQFRHPT VTPNPRANNP FRPSKVAPVQ
phim_p31    .......... .......... .......... .......... ..........

51                                                        100
phim_p62    PPAVRGTKAV ENCGPVAPRN KIVGGMEVTP HAYPWQVGLF IDDMYFCGGS
phim_p912   PPAVRGTKAV PNCGQ.SKST KIVGGGEVTP HAYPWQVGLF IDDMYFCGGS
phim5_1     PPAVRGTKAV ENCGPVAPKN KIVGGQEVTP HAYPWQVGLF IDDMYFCGGS
phim_p31    .......... .......... .......... .......... ..........

101                                                       150
phim_p62    IISDEWVLTA AHCMDGAGFV EVVMGAHSIH DETEATQVRA TSTDPFTHEN
phim_p912   IISEDWVLTA AHCMDGAGFV EVVMGAHKIH DDTEASRVSA ISTDFFTHEN
phim5_1     IISEDWVLTA AHCVDGAGFV EVVMGAHSIH DDTEASRISA TSTDFFTHEN
phim_p31    .......... .......... ...MGAHSIH DDTEASRVSA TSTDFFTHEN 151                                                       200
phim_p62    WNSPTLSNDL ALIKMPAPIE FNDVIQPVCL PTYTDASDDF VGESVTLTGW
phim_p912   WNSFLLTNDL ALIKMPAPIA FTDEIQPVCL PTYTDSDDDF VGESVTLTGW
phim5_1     WNSFTLTNDL ALIKMPAPIE FTPEIQPV.. .......... ..........
phim_p31    WNSFTLTNDL ALIKMPAPIE FTPEIQPVCL PSYTDAADDF IGESVVLTGW 201                                                       250
phim_p62    GKPSDSAFGI AEQLREVDVT TITTADCQAY YGIVTDKILC IDSEGGHGSC
phim_p912   GRASDSASGI SEVLREVDVT TITTADCQAY YGIVTDKILC IDSEGGHGSC
phim5_1     .......... .......... .......... .......... ..........
phim_p31    GRDSDAASGI SELLREVHVT TISTADCQAY YGIVTDKILC ISSEDGHGSC 251                                                       300
phim_p62    NGDSGGPMNY VTGGVTQTRG ITSFGSSTGC ETGYPDGYTR VTSYLDWIES
phim_p912   NGDSGGPMNY VTGGVTQTRG ITSFGSSTGC ETGYPDGYTR VTSYLDWIES
phim5_1     .......... .......... .......... .......... ..........
phim_p31    NGDSGGPMNY VTGGVTQTRG ITSFGSSTGC ETGYPDGYTR VTSYLDWIES 301
phim_p62    NTGIAIDP
phim_p912   NTGIAIDP
phim5_1     ........
phim_p31    NTGIAIDA
```

Figure 7

SEQUENCE LISTING

<160> NUMBER OF SEQ ID NOS: 25

<210> SEQ ID NO 1
<211> LENGTH: 943
<212> TYPE: DNA
<213> ORGANISM: homo sapiens

<400> SEQUENCE: 1

```
ctcttactcg cccttgtggc tgctgctagt gccgcagaat ggcgctggca gtttcgtcac      60
cctacagtga cccccaaccc tagggctaag aaccccttca gagtcaccaa aagctctcca     120
gtccaaccac cagcagtcag aggaacaaag gctgttgaga actgtggacc agtagcacca     180
aggaacaaga ttgtaggagg catggaggtg actccccatg cttacccctg gcaggtggga     240
cttttcattg atgatatgta cttctgtggt ggatcaatca tctccgacga atgggtcctt     300
acagctgctc actgtatgga tggtgctggg tttgttgagg ttgtgatggg tgctcacagt     360
atccatgacg aaactgaggc cacacaggtc cgtgccacat caactgattt cttcacccac     420
gagaactgga actccttcac cctctccaat gatcttgctc tcattaagat gccagcacca     480
```

-continued

| | |
|---|---|
| attgaattca acgatgtgat ccagcctgtc tgcctaccaa cctatactga tgctagtgat | 540 |
| gattttgttg gtgaatcagt cactcttact ggatgggta aaccatctga ctctgctttt | 600 |
| ggcatcgctg aacaacttcg tgaggttgat gtgacaacaa tcactactgc tgactgccag | 660 |
| gcatactacg gcattgtcac tgacaaaatc ctctgcatcg actccgaagg aggccatggt | 720 |
| tcctgcaatg gtgattccgg cgggccaatg aactatgtaa ctggtggtgt tactcagacc | 780 |
| cgtggtatta cctctttcgg atcctctacc ggctgcgaga ctggctaccc tgatggttac | 840 |
| acacgagtca ccagctatct ggactggatt gaatctaaca ctggcattgc cattgatcca | 900 |
| taaatacaat tctagcaaaa atacaataaa ttatacttaa atg | 943 |

<210> SEQ ID NO 2
<211> LENGTH: 599
<212> TYPE: DNA
<213> ORGANISM: homo sapiens

<400> SEQUENCE: 2

| | |
|---|---|
| gatgggtgct cacagtatcc atgacgatac tgaggcctct cgcgtcagtg ccacatcaac | 60 |
| tgatttcttc acccacgaga actggaactc cttcaccctc accaatgatc ttgctctcat | 120 |
| taagatgcca gcaccaattg aattcacacc tgaaattcaa cctgtctgcc taccaagcta | 180 |
| cactgatgct gctgatgatt tcattggtga atctgttgtc cttactggat ggggccgtga | 240 |
| ttctgatgct gcttccggca tctctgaact actccgtgag gttcatgtga ccacaatctc | 300 |
| cactgccgac tgccaggcat actacggcat tgtcactgac aaaatcctct gcatttcctc | 360 |
| tgaagacgga catggttctt gtaatgtga ttccggtggg ccaatgaact atgtaactgg | 420 |
| tggtgttact cagacccgtg gtattacctc cttcggatcc tctaccgggt gtgagactgg | 480 |
| ctaccctgat ggttacacac gtgtcaccag ctatctggac tggattgaat ctaacactgg | 540 |
| cattgccatt gatgcttgaa tataatacta gatatgtaat caaataaatt tcatgaatt | 599 |

<210> SEQ ID NO 3
<211> LENGTH: 943
<212> TYPE: DNA
<213> ORGANISM: homo sapiens

<400> SEQUENCE: 3

| | |
|---|---|
| ctcttactcg ccccttgtggc tgctgctagt gccgcagaat ggcgctggca gtttcgtcac | 60 |
| cctacagtga cccccaaccc tagggctaag aacccttca gagtcaccaa aagctctcca | 120 |
| gtccaaccac cagcagtcag aggaacaaag gctgttgaga actgtggacc agtagcacca | 180 |
| aggaacaaga ttgtaggagg catggaggtg actccccatg cttacccctg gcaggtggga | 240 |
| cttttcattg atgatatgta cttctgtggt ggatcaatca tctccgacga atgggtcctt | 300 |
| acagctgctc actgtatgga tggtgctggg tttgttgagg ttgtgatggg tgctcacagt | 360 |
| atccatgacg atactgaggc ctctcgcgtc agtgccacat caactgattt cttcacccac | 420 |
| gagaactgga actccttcac cctcaccaat gatcttgctc tcattaagat gccagcacca | 480 |
| attgaattca cacctgaaat tcaacctgtc tgcctaccaa gctacactga tgctgctgat | 540 |
| gatttcattg gtgaatctgt tgtccttact ggatggggcc gtgattctga tgctgcttcc | 600 |
| ggcatctctg aactactccg tgaggttcat gtgaccacaa tctccactgc cgactgccag | 660 |
| gcatactacg gcattgtcac tgacaaaatc ctctgcattt cctctgaaga cggacatggt | 720 |
| tcttgtaatg gtgattccgg tgggccaatg aactatgtaa ctggtggtgt tactcagacc | 780 |
| cgtggtatta cctccttcgg atcctctacc gggtgtgaga ctggctaccc tgatggttac | 840 |

```
acacgtgtca ccagctatct ggactggatt gaatctaaca ctggcattgc cattgatgct    900
tgaatataat actagatatg taatcaaata aatttcatga att                      943
```

<210> SEQ ID NO 4
<211> LENGTH: 300
<212> TYPE: PRT
<213> ORGANISM: homo sapiens

<400> SEQUENCE: 4

```
Leu Leu Leu Ala Leu Val Ala Ala Ser Ala Ala Glu Trp Arg Trp
  1               5                  10                  15

Gln Phe Arg His Pro Thr Val Thr Pro Asn Pro Arg Ala Lys Asn Pro
             20                  25                  30

Phe Arg Val Thr Lys Ser Ser Pro Val Gln Pro Pro Ala Val Arg Gly
         35                  40                  45

Thr Lys Ala Val Glu Asn Cys Gly Pro Val Ala Pro Arg Asn Lys Ile
     50                  55                  60

Val Gly Gly Met Glu Val Thr Pro His Ala Tyr Pro Trp Gln Val Gly
 65                  70                  75                  80

Leu Phe Ile Asp Asp Met Tyr Phe Cys Gly Ser Ile Ile Ser Asp
                 85                  90                  95

Glu Trp Val Leu Thr Ala Ala His Cys Met Asp Gly Ala Gly Phe Val
                100                 105                 110

Glu Val Val Met Gly Ala His Ser Ile His Asp Glu Thr Glu Ala Thr
                115                 120                 125

Gln Val Arg Ala Thr Ser Thr Asp Phe Phe Thr His Glu Asn Trp Asn
            130                 135                 140

Ser Phe Thr Leu Ser Asn Asp Leu Ala Leu Ile Lys Met Pro Ala Pro
145                 150                 155                 160

Ile Glu Phe Asn Asp Val Ile Gln Pro Val Cys Leu Pro Thr Tyr Thr
                165                 170                 175

Asp Ala Ser Asp Asp Phe Val Gly Glu Ser Val Thr Leu Thr Gly Trp
            180                 185                 190

Gly Lys Pro Ser Asp Ser Ala Phe Gly Ile Ala Glu Gln Leu Arg Glu
        195                 200                 205

Val Asp Val Thr Thr Ile Thr Thr Ala Asp Cys Gln Ala Tyr Tyr Gly
    210                 215                 220

Ile Val Thr Asp Lys Ile Leu Cys Ile Asp Ser Glu Gly Gly His Gly
225                 230                 235                 240

Ser Cys Asn Gly Asp Ser Gly Gly Pro Met Asn Tyr Val Thr Gly Gly
                245                 250                 255

Val Thr Gln Thr Arg Gly Ile Thr Ser Phe Gly Ser Ser Thr Gly Cys
            260                 265                 270

Glu Thr Gly Tyr Pro Asp Gly Tyr Thr Arg Val Thr Ser Tyr Leu Asp
        275                 280                 285

Trp Ile Glu Ser Asn Thr Gly Ile Ala Ile Asp Pro
    290                 295                 300
```

<210> SEQ ID NO 5
<211> LENGTH: 185
<212> TYPE: PRT
<213> ORGANISM: homo sapiens

<400> SEQUENCE: 5

```
Met Gly Ala His Ser Ile His Asp Asp Thr Glu Ala Ser Arg Val Ser
```

-continued

```
                1               5                      10                     15
        Ala Thr Ser Thr Asp Phe Phe Thr His Glu Asn Trp Asn Ser Phe Thr
                        20                     25                     30

Leu Thr Asn Asp Leu Ala Leu Ile Lys Met Pro Ala Pro Ile Glu Phe
                        35                     40                     45

Thr Pro Glu Ile Gln Pro Val Cys Leu Pro Ser Tyr Thr Asp Ala Ala
                50                     55                     60

Asp Phe Ile Gly Glu Ser Val Val Leu Thr Gly Trp Gly Arg Asp
        65                      70                     75                     80

Ser Asp Ala Ala Ser Gly Ile Ser Glu Leu Arg Glu Val His Val
                        85                     90                     95

Thr Thr Ile Ser Thr Ala Asp Cys Gln Ala Tyr Tyr Gly Ile Val Thr
                       100                    105                    110

Asp Lys Ile Leu Cys Ile Ser Ser Glu Asp Gly His Gly Ser Cys Asn
                       115                    120                    125

Gly Asp Ser Gly Gly Pro Met Asn Tyr Val Thr Gly Gly Val Thr Gln
                130                    135                    140

Thr Arg Gly Ile Thr Ser Phe Gly Ser Ser Thr Gly Cys Glu Thr Gly
        145                    150                    155                    160

Tyr Pro Asp Gly Tyr Thr Arg Val Thr Ser Tyr Leu Asp Trp Ile Glu
                       165                    170                    175

Ser Asn Thr Gly Ile Ala Ile Asp Ala
                       180                    185

<210> SEQ ID NO 6
<211> LENGTH: 300
<212> TYPE: PRT
<213> ORGANISM: homo sapiens

<400> SEQUENCE: 6

Leu Leu Leu Ala Leu Val Ala Ala Ser Ala Ala Glu Trp Arg Trp
         1              5                      10                     15

Gln Phe Arg His Pro Thr Val Thr Pro Asn Pro Arg Ala Lys Asn Pro
                        20                     25                     30

Phe Arg Val Thr Lys Ser Ser Pro Val Gln Pro Pro Ala Val Arg Gly
                        35                     40                     45

Thr Lys Ala Val Glu Asn Cys Gly Pro Val Ala Pro Arg Asn Lys Ile
                50                     55                     60

Val Gly Gly Met Glu Val Thr Pro His Ala Tyr Pro Trp Gln Val Gly
        65                      70                     75                     80

Leu Phe Ile Asp Asp Met Tyr Phe Cys Gly Gly Ser Ile Ile Ser Asp
                        85                     90                     95

Glu Trp Val Leu Thr Ala Ala His Cys Met Asp Gly Ala Gly Phe Val
                       100                    105                    110

Glu Val Val Met Gly Ala His Ser Ile His Asp Asp Thr Glu Ala Ser
                       115                    120                    125

Arg Val Ser Ala Thr Ser Thr Asp Phe Thr His Glu Asn Trp Asn
                130                    135                    140

Ser Phe Thr Leu Thr Asn Asp Leu Ala Leu Ile Lys Met Pro Ala Pro
        145                    150                    155                    160

Ile Glu Phe Thr Pro Glu Ile Gln Pro Val Cys Leu Pro Ser Tyr Thr
                       165                    170                    175

Asp Ala Ala Asp Asp Phe Ile Gly Glu Ser Val Val Leu Thr Gly Trp
                       180                    185                    190
```

Gly Arg Asp Ser Asp Ala Ala Ser Gly Ile Ser Glu Leu Leu Arg Glu
            195                 200                 205

Val His Val Thr Thr Ile Ser Thr Ala Asp Cys Gln Ala Tyr Tyr Gly
        210                 215                 220

Ile Val Thr Asp Lys Ile Leu Cys Ile Ser Ser Glu Asp Gly His Gly
225                 230                 235                 240

Ser Cys Asn Gly Asp Ser Gly Gly Pro Met Asn Tyr Val Thr Gly Gly
                245                 250                 255

Val Thr Gln Thr Arg Gly Ile Thr Ser Phe Gly Ser Ser Thr Gly Cys
            260                 265                 270

Glu Thr Gly Tyr Pro Asp Gly Tyr Thr Arg Val Thr Ser Tyr Leu Asp
        275                 280                 285

Trp Ile Glu Ser Asn Thr Gly Ile Ala Ile Asp Ala
290                 295                 300

<210> SEQ ID NO 7
<211> LENGTH: 536
<212> TYPE: DNA
<213> ORGANISM: homo sapiens

<400> SEQUENCE: 7
cccgggcagg tccaggatcg ccctcttact tgcccttgtg gctgctacag ctagtgcttc      60
agaatggcgc tggcagttcc gtcaccccac tgtgaccccc aaccccagag ctaacaaccc     120
cttcagaccc agtaaagtcg ctccagtcca accaccagca gtcagaggaa caaaggctgt     180
tgagaactgt ggaccagtag caccaaagaa caagattgta ggagggcaag aagtgactcc     240
ccatgcttac ccctggcagg tgggactctt catcgatgac atgtacttct gcggtggatc     300
catcatctca gaggactggg tgcttacagc tgctcactgt gtggatggtg ctggttttgt     360
cgaagttgtg atgggtgctc acagtatcca tgacgatact gaggcctctc gcatcagtgc     420
cacatcaact gatttcttca cccacgagaa ctggaactcc ttcaccctca ccaatgatct     480
tgctctcatt aagatgccag cacccattga gttcacacct gaaattcaac ctgtct        536

<210> SEQ ID NO 8
<211> LENGTH: 178
<212> TYPE: PRT
<213> ORGANISM: homo sapiens

<400> SEQUENCE: 8

Pro Gly Arg Ser Arg Ile Ala Leu Leu Leu Ala Leu Val Ala Ala Thr
1               5                   10                  15

Ala Ser Ala Ser Glu Trp Arg Trp Gln Phe Arg His Pro Thr Val Thr
            20                  25                  30

Pro Asn Pro Arg Ala Asn Asn Pro Phe Arg Pro Ser Lys Val Ala Pro
        35                  40                  45

Val Gln Pro Pro Ala Val Arg Gly Thr Lys Ala Val Glu Asn Cys Gly
    50                  55                  60

Pro Val Ala Pro Lys Asn Lys Ile Val Gly Gly Gln Glu Val Thr Pro
65                  70                  75                  80

His Ala Tyr Pro Trp Gln Val Gly Leu Phe Ile Asp Asp Met Tyr Phe
                85                  90                  95

Cys Gly Gly Ser Ile Ile Ser Glu Asp Trp Val Leu Thr Ala Ala His
            100                 105                 110

Cys Val Asp Gly Ala Gly Phe Val Glu Val Val Met Gly Ala His Ser
        115                 120                 125

Ile His Asp Asp Thr Glu Ala Ser Arg Ile Ser Ala Thr Ser Thr Asp
            130                 135                 140

Phe Phe Thr His Glu Asn Trp Asn Ser Phe Thr Leu Thr Asn Asp Leu
145                 150                 155                 160

Ala Leu Ile Lys Met Pro Ala Pro Ile Glu Phe Thr Pro Glu Ile Gln
                165                 170                 175

Pro Val

<210> SEQ ID NO 9
<211> LENGTH: 968
<212> TYPE: DNA
<213> ORGANISM: homo sapiens

<400> SEQUENCE: 9

| cccgggcagg | tccaggatcg | ccctcttact | tgcccttgtg | gctgctacag | ctagtgcttc | 60 |
| agaatggcgc | tggcagttcc | gtcaccccac | tgtgacccccc | aacccagag | ctaacaaccc | 120 |
| cttcagaccc | agtaaagtcg | ctccagtcca | accaccagca | gtcagaggaa | caaaggctgt | 180 |
| tgagaactgt | ggaccagtag | caccaaagaa | caagattgta | ggagggcaag | aagtgactcc | 240 |
| ccatgcttac | ccctggcagg | tgggactctt | catcgatgac | atgtacttct | gcggtggatc | 300 |
| catcatctca | gaggactggg | tgcttacagc | tgctcactgt | gtggatggtg | ctggttttgt | 360 |
| cgaagttgtg | atgggtgctc | acagtatcca | tgacgatact | gaggcctctc | gcgtcagtgc | 420 |
| cacatcaact | gatttcttca | cccacgagaa | ctggaactcc | ttcaccctca | ccaatgatct | 480 |
| tgctctcatt | aagatgccag | caccaattga | attcacacct | gaaattcaac | ctgtctgcct | 540 |
| accaagctac | actgatgctg | ctgatgattt | cattggtgaa | tctgttgtcc | ttactggatg | 600 |
| gggccgtgat | tctgatgctg | cttccggcat | ctctgaacta | ctccgtgagg | ttcatgtgac | 660 |
| cacaatctcc | actgccgact | gccaggcata | ctacggcatt | gtcactgaca | aaatcctctg | 720 |
| catttcctct | gaagacggac | atggttcttg | taatggtgat | tccgtgggc | caatgaacta | 780 |
| tgtaactggt | ggtgttactc | agacccgtgg | tattacctcc | ttcggatcct | ctaccgggtg | 840 |
| tgagactggc | taccctgatg | ttacacacg | tgtcaccagc | tatctggact | ggattgaatc | 900 |
| taacactggc | attgccattg | atgcttgaat | ataatactag | atatgtaatc | aaataaattt | 960 |
| catgaatt | | | | | | 968 |

<210> SEQ ID NO 10
<211> LENGTH: 308
<212> TYPE: PRT
<213> ORGANISM: homo sapiens

<400> SEQUENCE: 10

Pro Gly Arg Ser Arg Ile Ala Leu Leu Leu Ala Leu Val Ala Ala Thr
1               5                   10                  15

Ala Ser Ala Ser Glu Trp Arg Trp Gln Phe Arg His Pro Thr Val Thr
                20                  25                  30

Pro Asn Pro Arg Ala Asn Asn Pro Phe Arg Pro Ser Lys Val Ala Pro
            35                  40                  45

Val Gln Pro Pro Ala Val Arg Gly Thr Lys Ala Val Glu Asn Cys Gly
        50                  55                  60

Pro Val Ala Pro Lys Asn Lys Ile Val Gly Gly Gln Glu Val Thr Pro
65                  70                  75                  80

His Ala Tyr Pro Trp Gln Val Gly Leu Phe Ile Asp Asp Met Tyr Phe
                85                  90                  95

```
Cys Gly Gly Ser Ile Ile Ser Glu Asp Trp Val Leu Thr Ala Ala His
                100                 105                 110
Cys Val Asp Gly Ala Gly Phe Val Glu Val Val Met Gly Ala His Ser
            115                 120                 125
Ile His Asp Asp Thr Glu Ala Ser Arg Val Ser Ala Thr Ser Thr Asp
130                 135                 140
Phe Phe Thr His Glu Asn Trp Asn Ser Phe Thr Leu Thr Asn Asp Leu
145                 150                 155                 160
Ala Leu Ile Lys Met Pro Ala Pro Ile Glu Phe Thr Pro Glu Ile Gln
                165                 170                 175
Pro Val Cys Leu Pro Ser Tyr Thr Asp Ala Ala Asp Asp Phe Ile Gly
            180                 185                 190
Glu Ser Val Val Leu Thr Gly Trp Gly Arg Asp Ser Asp Ala Ala Ser
            195                 200                 205
Gly Ile Ser Glu Leu Leu Arg Glu Val His Val Thr Thr Ile Ser Thr
210                 215                 220
Ala Asp Cys Gln Ala Tyr Tyr Gly Ile Val Thr Asp Lys Ile Leu Cys
225                 230                 235                 240
Ile Ser Ser Glu Asp Gly His Gly Ser Cys Asn Gly Asp Ser Gly Gly
                245                 250                 255
Pro Met Asn Tyr Val Thr Gly Gly Val Thr Gln Thr Arg Gly Ile Thr
            260                 265                 270
Ser Phe Gly Ser Ser Thr Gly Cys Glu Thr Gly Tyr Pro Asp Gly Tyr
            275                 280                 285
Thr Arg Val Thr Ser Tyr Leu Asp Trp Ile Glu Ser Asn Thr Gly Ile
            290                 295                 300
Ala Ile Asp Ala
305

<210> SEQ ID NO 11
<211> LENGTH: 11
<212> TYPE: PRT
<213> ORGANISM: homo sapiens

<400> SEQUENCE: 11

Ala Val Glu Asn Cys Gly Pro Val Ala Pro Arg
1               5                   10

<210> SEQ ID NO 12
<211> LENGTH: 13
<212> TYPE: PRT
<213> ORGANISM: homo sapiens

<400> SEQUENCE: 12

Ala Val Glu Asn Cys Gly Pro Val Ala Pro Arg Asn Lys
1               5                   10

<210> SEQ ID NO 13
<211> LENGTH: 14
<212> TYPE: PRT
<213> ORGANISM: homo sapiens

<400> SEQUENCE: 13

Gly Thr Lys Ala Val Glu Asn Cys Gly Pro Val Ala Pro Arg
1               5                   10

<210> SEQ ID NO 14
<211> LENGTH: 16
<212> TYPE: PRT
```

<210> ORGANISM: homo sapiens

<400> SEQUENCE: 14

Gly Thr Lys Ala Val Glu Asn Cys Gly Pro Val Ala Pro Arg Asn Lys
1               5                   10                  15

<210> SEQ ID NO 15
<211> LENGTH: 24
<212> TYPE: PRT
<213> ORGANISM: homo sapiens

<400> SEQUENCE: 15

Ser Ser Pro Val Gln Pro Pro Ala Val Arg Gly Thr Lys Ala Val Glu
1               5                   10                  15

Asn Cys Gly Pro Val Ala Pro Arg
            20

<210> SEQ ID NO 16
<211> LENGTH: 26
<212> TYPE: PRT
<213> ORGANISM: homo sapiens

<400> SEQUENCE: 16

Ser Ser Pro Val Gln Pro Pro Ala Val Arg Gly Thr Lys Ala Val Glu
1               5                   10                  15

Asn Cys Gly Pro Val Ala Pro Arg Asn Lys
            20                  25

<210> SEQ ID NO 17
<211> LENGTH: 17
<212> TYPE: DNA
<213> ORGANISM: homo sapiens
<220> FEATURE:
<221> NAME/KEY: misc_feature
<222> LOCATION: (1)...(17)
<223> OTHER INFORMATION: n = A,T,C or G

<400> SEQUENCE: 17
cacgcctacc cntggca                                                      17

<210> SEQ ID NO 18
<211> LENGTH: 21
<212> TYPE: DNA
<213> ORGANISM: homo sapiens

<400> SEQUENCE: 18
gtgttggact cgatccagat c                                                 21

<210> SEQ ID NO 19
<211> LENGTH: 633
<212> TYPE: DNA
<213> ORGANISM: homo sapiens

<400> SEQUENCE: 19
cacgcctacc cgtggcaggt gggacttttc attgatgata tgtacttctg tggaggatca      60
atcatctccg acgaatgggt ccttacagct gctcactgta tggatggtgc tggatttgtt     120
gaggttgtga tgggtgctca cagtatccat gacgaaactg aggccacaca ggtccgtgcc     180
acatcaactg atttcttcac acacgagaac tggaactcct tcaccctctc caatgatctt     240
gctctcatta agatgccagc accaattgaa ttcaacgatg tgatccagcc tgtctgccta     300
ccaacctata ctgatgccag tgatgatttt gttggtgaat cagtcactct tactggatgg     360

-continued

```
ggtaaaccat ctgactctgc ttttggcatc gctgaacaac ttcgtgaggt tgatgtgaca      420
acaatcacta ctgctgactg ccaggcatac tacggcattg tcactgacaa aatcctctgc      480
atcgactccg aaggaggcca tggttcctgc aatggtgatt ccgtgggcc aatgaactat       540 gtaactggtg tgttactca gacccgtggt attacctctt tcggatcctc taccggctgc      600
gagactgggt accctgataa ttacacacga gtc                                   633
```

<210> SEQ ID NO 20
<211> LENGTH: 211
<212> TYPE: PRT
<213> ORGANISM: homo sapiens

<400> SEQUENCE: 20

```
His Ala Tyr Pro Trp Gln Val Gly Leu Phe Ile Asp Asp Met Tyr Phe
 1               5                  10                  15

Cys Gly Gly Ser Ile Ile Ser Asp Glu Trp Val Leu Thr Ala Ala His
                20                  25                  30

Cys Met Asp Gly Ala Gly Phe Val Glu Val Val Met Gly Ala His Ser
            35                  40                  45

Ile His Asp Glu Thr Glu Ala Thr Gln Val Arg Ala Thr Ser Thr Asp
        50                  55                  60

Phe Phe Thr His Glu Asn Trp Asn Ser Phe Thr Leu Ser Asn Asp Leu
 65                 70                  75                  80

Ala Leu Ile Lys Met Pro Ala Pro Ile Glu Phe Asn Asp Val Ile Gln
                85                  90                  95

Pro Val Cys Leu Pro Thr Tyr Thr Asp Ala Ser Asp Asp Phe Val Gly
            100                 105                 110

Glu Ser Val Thr Leu Thr Gly Trp Gly Lys Pro Ser Asp Ser Ala Phe
        115                 120                 125

Gly Ile Ala Glu Gln Leu Arg Glu Val Asp Val Thr Thr Ile Thr Thr
    130                 135                 140

Ala Asp Cys Gln Ala Tyr Tyr Gly Ile Val Thr Asp Lys Ile Leu Cys
145                 150                 155                 160

Ile Asp Ser Glu Gly Gly His Gly Ser Cys Asn Gly Asp Ser Gly Gly
                165                 170                 175

Pro Met Asn Tyr Val Thr Gly Val Thr Gln Thr Arg Gly Ile Thr
            180                 185                 190

Ser Phe Gly Ser Ser Thr Gly Cys Glu Thr Gly Tyr Pro Asp Asn Tyr
        195                 200                 205

Thr Arg Val
    210
```

<210> SEQ ID NO 21
<211> LENGTH: 967
<212> TYPE: DNA
<213> ORGANISM: homo sapiens

<400> SEQUENCE: 21

```
atcgccctct tactcgccct tgtggctgcc actgctagtg cttcagaatg gcgctggcag       60
ttccgtcacc ccaccgtgac ccccaacccc agagctaaca accccttcag accaagtaaa      120
gttgctccag tccaaccacc agcagtcaga ggaacaaagg ctgtacccaa ctgtggacag      180
tcaaagtcta ccaagattgt aggaggtggt gaggtaactc cccatgctta cccctgcag       240 gtgggacttt tcattgatga catgtacttc tgcggkggat ccatcatctc agaggactgg      300
gtccttacag ctgctcactg tatggatggt gctgggtttg ttgaggttgt gatgggtgct      360
```

-continued

```
cacaagatcc atgatgatac tgaggcctct cgcgtcagtg ccatatcaac tgatttcttc    420
acccacgaga actggaactc cttccttctc accaatgatc ttgctctcat taagatgcca    480
gcacccattg cattcactga tgagatccag cctgtatgcc tgccaaccta cactgactcc    540
gatgatgatt tgttggtga atcagtcact cttactggct ggggtcgtgc atctgactct     600
gctagcggca tctctgaagt acttcgtgag gttgatgtga caacaataac tactgccgac    660
tgccaggcat actatggtat tgtcactgac aaaatcctct gcatcgactc agaaggaggt    720
catgggtctt gcaatggtga ttccggtggg ccaatgaact atgtaactgg tggtgttact    780
cagacccgtg gtattacctc cttcggatcc tctaccggct gtgagactgg ctaccctgat    840
ggttacacac gagtcaccag ctatctagac tggattgaat ctaacactgg cattgccatt    900
gatccttgaa taatattcta gctgaatgat aataaattca tgattgataa tcaaaaaaaa    960
aaaaaaa                                                              967
```

<210> SEQ ID NO 22
<211> LENGTH: 302
<212> TYPE: PRT
<213> ORGANISM: homo sapiens

<400> SEQUENCE: 22

```
Ile Ala Leu Leu Leu Ala Leu Val Ala Ala Thr Ala Ser Ala Ser Glu
 1               5                  10                  15

Trp Arg Trp Gln Phe Arg His Pro Thr Val Thr Pro Asn Pro Arg Ala
            20                  25                  30

Asn Asn Pro Phe Arg Pro Ser Lys Val Ala Pro Val Gln Pro Pro Ala
        35                  40                  45

Val Arg Gly Thr Lys Ala Val Pro Asn Cys Gly Gln Ser Lys Ser Thr
    50                  55                  60

Lys Ile Val Gly Gly Glu Val Thr Pro His Ala Tyr Pro Trp Gln
65                  70                  75                  80

Val Gly Leu Phe Ile Asp Asp Met Tyr Phe Cys Gly Gly Ser Ile Ile
                85                  90                  95

Ser Glu Asp Trp Val Leu Thr Ala Ala His Cys Met Asp Gly Ala Gly
            100                 105                 110

Phe Val Glu Val Val Met Gly Ala His Lys Ile His Asp Asp Thr Glu
        115                 120                 125

Ala Ser Arg Val Ser Ala Ile Ser Thr Asp Phe Phe Thr His Glu Asn
    130                 135                 140

Trp Asn Ser Phe Leu Leu Thr Asn Asp Leu Ala Leu Ile Lys Met Pro
145                 150                 155                 160

Ala Pro Ile Ala Phe Thr Asp Glu Ile Gln Pro Val Cys Leu Pro Thr
                165                 170                 175

Tyr Thr Asp Ser Asp Asp Phe Val Gly Glu Ser Val Thr Leu Thr
            180                 185                 190

Gly Trp Gly Arg Ala Ser Asp Ser Ala Ser Gly Ile Ser Glu Val Leu
        195                 200                 205

Arg Glu Val Asp Val Thr Thr Ile Thr Thr Ala Asp Cys Gln Ala Tyr
    210                 215                 220

Tyr Gly Ile Val Thr Asp Lys Ile Leu Cys Ile Asp Ser Glu Gly Gly
225                 230                 235                 240

His Gly Ser Cys Asn Gly Asp Ser Gly Gly Pro Met Asn Tyr Val Thr
                245                 250                 255
```

```
Gly Gly Val Thr Gln Thr Arg Gly Ile Thr Ser Phe Gly Ser Ser Thr
            260                 265                 270

Gly Cys Glu Thr Gly Tyr Pro Asp Gly Tyr Thr Arg Val Thr Ser Tyr
        275                 280                 285

Leu Asp Trp Ile Glu Ser Asn Thr Gly Ile Ala Ile Asp Pro
    290                 295                 300
```

<210> SEQ ID NO 23
<211> LENGTH: 535
<212> TYPE: DNA
<213> ORGANISM: homo sapiens

<400> SEQUENCE: 23

```
cccgggcagg tccaggatcg ccctcttact tgcccttgtg gctgctacag ctagtgcttc     60
agaatggcgc tggcagttcc gtcaccccac tgtgaccccc aacccagag ctaacaaccc    120
cttcagaccc agtaaagtcg ctccagttca accaccagca gtcagaggaa caaaggctgt   180
tgagaactgt ggaccagtag caccaaagaa caagattgta ggagggcaag aagtgactcc   240
ccatgcttac ccctggcagg tgggactctt catcgatgac atgtacttct tcggtggatc   300
catcatctca gaggactggg tcgttacagc tcgtcactgt atggatggtc gtggttttgt   360
cgaagttgtg atgggtgctc acagtatcct agacgatact gaggcctctc gcatgagtgc   420
cacatcaact gatttcttca cccacgagaa ctggaactcc ttcaccctca ccaatgatct   480
tgctctcatt aagatgccag cacccattga gttcacacct gaaattcaac ctgtc        535
```

<210> SEQ ID NO 24
<211> LENGTH: 178
<212> TYPE: PRT
<213> ORGANISM: homo sapiens

<400> SEQUENCE: 24

```
Pro Gly Arg Ser Arg Ile Ala Leu Leu Ala Leu Val Ala Ala Thr
  1               5                  10                  15

Ala Ser Ala Ser Glu Trp Arg Trp Gln Phe Arg His Pro Thr Val Thr
                 20                 25                  30

Pro Asn Pro Arg Ala Asn Asn Pro Phe Arg Pro Ser Lys Val Ala Pro
            35                  40                  45

Val Gln Pro Pro Ala Val Arg Gly Thr Lys Ala Val Glu Asn Cys Gly
 50                  55                  60

Pro Val Ala Pro Lys Asn Lys Ile Val Gly Gln Glu Val Thr Pro
 65                  70                  75                  80

His Ala Tyr Pro Trp Gln Val Gly Leu Phe Ile Asp Asp Met Tyr Phe
                 85                  90                  95

Phe Gly Gly Ser Ile Ile Ser Glu Asp Trp Val Val Thr Ala Arg His
                100                 105                 110

Cys Met Asp Gly Arg Gly Phe Val Glu Val Val Met Gly Ala His Ser
            115                 120                 125

Ile Leu Asp Asp Thr Glu Ala Ser Arg Met Ser Ala Thr Ser Thr Asp
            130                 135                 140

Phe Phe Thr His Glu Asn Trp Asn Ser Phe Thr Leu Thr Asn Asp Leu
145                 150                 155                 160

Ala Leu Ile Lys Met Pro Ala Pro Ile Glu Phe Thr Pro Glu Ile Gln
                165                 170                 175

Pro Val
```

```
<210> SEQ ID NO 25
<211> LENGTH: 9
<212> TYPE: PRT
<213> ORGANISM: homo sapiens

<400> SEQUENCE: 25

Ala Val Glu Asn Cys Gly Pro Val Ala
 1               5
```

ENZYME AND DNA SEQUENCE ENCODING KRILL-DERIVED MULTIFUNCTIONAL PROTEIN

This is a Section 371 National Stage of Application No. PCT/US97/15197, filed Aug. 28, 1997, which claims priority of U.S. application Ser. No. 08/705,875, filed Aug. 28, 1996, now U.S. Pat. No. 6,040,155, and U.S. application Ser. No. 08/768,318, filed Dec. 17, 1996, now abandoned.

The present invention relates to purified nucleic acids encoding a krill-derived enzymes such as proteinases, which can be a multifunctional protein, and to purified polypeptides. A protein having "multifunctional activity," is defined herein as including at least one of a chymotrypsin, trypsin, collagenase, elastase or exo peptidase activity, or asialo $GM_1$ ceramide binding activity.

Multifunctional proteins are useful for multiple purposes, including treating viral infections such as herpes outbreaks, fungal, bacterial or parasitic infections, including the primary and secondary infections of leprosy, colitis, ulcers, hemorrhoids, corneal scarring, dental plaque, acne, cystic fibrosis, blood clots, wounds, immune disorders including autoimmune disease, such as lupus erythematosus and multiple sclerosis, and cancer. Purified polypeptides having proteinase or multifunctional activity and purified nucleic acids encoding such polypeptides are desirable to provide pharmaceutically useful products. Other uses for proteinases are well recognized in the art and include digesting proteinaceous material for a variety of purposes including cleaning and creating improved feeds for animals or bacteriology.

SUMMARY OF THE INVENTION

Until now, sequences encoding krill-derived proteinases similar to those set forth in the Sequence Listing have not been identified. The amino acid sequence included in SEQ ID NOS:4, 5, 6, 10, 20 22 or 24 or other isoforms thereof or chimeric polypeptides thereof are examples of such enzymes. In particular, in many cases the invention is specified in terms of a reference protein sequence which is AA64-300 of SEQ ID NO:4 or a sequence differing therefrom by at least one of the residue differences found in SEQ ID NOS:5, 20, 22, or 24. In an embodiment of the invention, the reference reference sequence further has the differences relative to SEQ ID NO: 4 that are found in SEQ ID NO:8. These differences are illustrated in FIGS. 5 and 6.

One preferred embodiment of the present invention is a substantially pure nucleic acid comprising a nucleic acid encoding a polypeptide having at least about 70% homology (such as identity or similarity) to a krill-derived multifunctional protein or a reference protein, such as the polypeptide of SEQ ID NOS:4, 5, 6, 8, 10, 20, 22 or 24 and in one embodiment especially SEQ ID NOS:4, 6, 10 or 22, and more preferably, at least about 80% homology, and most preferably, at least about 90% homology. Preferably, In another embodiment embodiment, the homology is with reference to SEQ ID NOS:4, 5, 20, 22 or 24. Even more preferably, the nucleic acid comprises a nucleic acid encoding a polypeptide sharing at least about 70% amino acid identity with a reference protein or, a krill-derived multifunctional protein, and yet more preferably, at least about 80% identity, and still more preferably, at least about 90% identity. Yet still more preferably, the homology or identity is at least about 95%. These levels of homology (such as identity apply to all embodiments of the invention.

In certain preferred embodiments, the substantially pure nucleic acid comprises an engineered nucleic acid variant encoding a polypeptide differing from a reference protein or a krill-derived multifunctional protein or its isoforms by no more than about 33 amino acid substitutions. and more preferably, no more than about 20 amino acid substitutions. Preferably, the engineered substitutions cause a conservative substitution in the amino acid sequence of a reference sequence or a multifunctional protein.

Preferred substantially pure nucleic acids also include nucleic acid analogs. In certain preferred embodiments, the nucleic acid comprises the open reading frames of SEQ ID NOS:1, 2, 3, 7, 9, 19, 21 or 23 and more preferably, SEQ ID NOS:1, 3, 9 or 22. In another aspect, the nucleic acid includes base pairs 190–900 of SEQ ID NO:1, base pairs 2–556 of SEQ ID NO:2, base pairs 190–900 of SEQ ID NO:3, base pairs 215–925 of SEQ ID NO:9, base pairs 1–633 of SEQ ID NO:19, base pairs 196–906 of SEQ ID NO:21, or base pairs 215–535 of SEQ ID NO:23 (in one embodiment, 1–900 of SEQ ID NO:1, base pairs 2–556 of SEQ ID NO:2, base pairs 1–900 of SEQ ID NO:3, base pairs 2–925 of SEQ ID NO:9, base pairs 1–633 of SEQ ID NO:19, base pairs 1–906 of SEQ ID NO:21, or base pairs 2–535 of SEQ ID NO:23), or more preferably base pairs 190–900 of SEQ ID NO:1, base pairs 2–556 of SEQ ID NO:2, base pairs 1–633 of SEQ ID NO: 19 base pairs 196–906 of SEQ ID NO:21 or base pairs 215–535 of SEQ ID NO:23. The invention additionally includes vectors capable of reproducing in a cell (such as a eukaryotic or prokaryotic cell) having a nucleic acid described above as well as transformed cells having such nucleic acid. Further, the invention includes a substantially pure nucleic acid comprising a nucleic acid that hybridizes, under stringent conditions, to a nucleic acid encoding a polypeptide having at least about 70% homology to a reference sequence or a krill-derived multifunctional protein, such as the polypeptide of SEQ ID NOS:4, 5, 6, 8, 10, 20, 22 or 24 and more preferably, SEQ ID NOS:4, 6, 10 or 22.

In one embodiment, the nucleic acid is a reference nucleic acid sequence including the open reading frame sequence of SEQ ID NO:1 (or preferably preferably the portion from the $NH_2$-IleValGlyGlyMet sequence through to the end) or a sequence differing therefrom by at least one of the bp differences found in SEQ ID NOS:2, 19, 21 or 23 (or preferably preferably the portion from the $NH_2$-IleValGlyGly sequence through to the end). In one embodiment, the nucleic acid includes a sequence with about 50%, about 60%, about 70%, about 80%, about 90% or about 95% identity to a reference sequence.

Another preferred embodiment is a transformed cell (such as a prokaryotic or eukaryotic cell) comprising a nucleic acid encoding a polypeptide having at least about 70% homology to a reference sequence or a krill-derived multifunctional protein. Preferably, the transformed cell expresses one of the enzymes described herein.

Yet another preferred embodiment is a vector capable of reproducing in a cell such as a eukaryotic or prokaryotic cell, the vector comprising a nucleic acid encoding a polypeptide having at least about 70% homology to a reference sequence or a krill-derived multifunctional protein. Preferably, the inventive vector codes for expression, intracellularly or extracellularly, of one of the multifunctional proteins described herein.

Another embodiment of the present invention is a polypeptide comprising a substantially pure isoform of a reference sequence or a krill-derived multifunctional protein or engineered variant thereof, and preferably, a polypeptide comprising SEQ ID NOS:4, 5, 6, 8, 10, 20, 22 or 24 and especially, SEQ ID NOS:4, 6, 10 or 22. In one embodiment, the isoform is a polypeptide comprising SEQ ID NOS:4, 5, 20, 22 or 24. The invention further provides a pharmaceutical composition for treating an animal comprising an effective amount of such a polypeptide together with a pharmaceutically acceptable carrier.

Yet another preferred embodiment is a method of preparing an enzyme such as a multifunctional protein, wherein the protein has at least about 70% homology to a reference sequence or a krill-derived multifunctional protein. Such method comprises (a) transforming an appropriate eukaryotic or prokaryotic cell with an expression vector for expressing intracellularly or extracellularly a nucleic acid encoding the protein;

(b) growing the transformed cell in culture; and (c) isolating the protein from the transformed cell or the culture medium.

Yet another preferred embodiment is a pharmaceutical composition for treating an animal comprising an effective amount of an expression vector comprising a nucleic acid encoding a multifunctional protein, and a pharmaceutically acceptable carrier. The invention further provides a pharmaceutical composition for treating an animal comprising an effective amount of a nucleic acid encoding a polypeptide having at least about 70% homology to a reference sequence or a krill-derived multifunctional protein.

BRIEF DESCRIPTION OF THE DRAWINGS

FIG. 1 shows the DNA sequence of a first isoform ("p62") (SEQ ID NO:1) of a krill-derived multifunctional protein aligned with the DNA sequence of a second isoform ("p31") (SEQ ID NO:2).

FIG. 2 shows the amino acid sequence of the first isoform ("p62") (SEQ ID NO:4) of a krill-derived multifunctional protein aligned with the amino acid sequence of the second isoform ("p31") (SEQ ID NO:5).

FIG. 3 shows the DNA sequence of a third isoform ("p5.1a") (SEQ ID NO:7) of a krill-derived multifunctional protein aligned with the DNA sequence of the first isoform ("p62") (SEQ ID NO: 1).

FIG. 4 shows the amino acid sequence of the third isoform ("p5.1a") (SEQ ID NO:8) aligned with the amino acid sequence of the first isoform ("p62") (SEQ ID NO:4) and the amino acid sequence of the second isoform ("p31") (SEQ ID NO:5).

FIG. 5 shows sequence comparisons between the nucleic acid sequences for p62 (SEQ in NO: 1), p 13 (SEQ ID NO:19), p912 (SEQ ID NO:21), p5.1b (SEQ ID NO:23) and p31 (SEQ ID NO:2), as well as sequence comparisons comparisons for the aligned peptide sequences (SEQ ID NOS:4, 20, 22, 24 and 5, respectively). Nucleic Nucleic acid sequence differences in the open reading frames relative to p62 are indicated by underlining, and differences in amino acid sequence are indicate with recitals of the differing residues.

FIG. 6 shows sequence comparisons between the polypeptide sequences encoded by p62 (SEQ ID NO: 4), p13 (SEQ ID NO:20), p912 (SEQ ID NO:22), p5.1b (SEQ ID NO:24) and p31 (SEQ ID NO:5).

FIG. 7 illustrates a sequence alignment between the polypeptide sequences encoded by p62 (SEQ ID NO:4), p912 (SEQ ID NO:22), p5.1a (SEQ ID NO:8) and p31 (SEQ ID NO:5).

DETAILED DESCRIPTION

For the purposes of this application, the terms listed below shall have the following meaning:

enzymatically active segment

A segment of a multifunctional protein having activity comprising at least one of a chymotrypsin, trypsin, collagenase, elastase or exo peptidase activity.

hydrolase

An enzyme that degrades bonds formed by dehydration reactions such as amide, ester, or ether bonds. The term encompasses, but is not limited to, proteases such as trypsin and chymotrypsin.

isoform

A naturally occurring sequence variant of a substantially homologous protein within the same organism. Preferably, the isoform shares at least about 80% identity and more preferably, at least about 85% identity with SEQ. ID NO:4.

krill-derived multifunctional protein

A multifunctional protein having the same sequence as a protein isolated from krill having the properties of the protein described in the section entitled "Preferred Characteristics of the Multifunctional Protein." This protein is also referred to as the "krill-derived multifunctional hydrolase" and includes all isoforms of the protein. The amino acid sequence included in SEQ ID NO:4, SEQ ID NO:5, SEQ ID NO:6, SEQ ID NO:8 or SEQ ID NO:10 or other isoforms thereof or chimeric polypeptides thereof are examples of krill-derived multifunctional proteins.

multifunctional protein

A protein having activity comprising at least one of a chymotrypsin, trypsin, collagenase, elastase or exo peptidase activity or asialo $GM_1$ ceramide binding activity, and substantial homology to at least a segment of a krill-derived multifunctional protein.

nucleic acid

The nucleic acid sequence embodiments of the invention are preferably deoxyribonucleic acid sequences, preferably double-stranded deoxyribonucleic acid sequences. However, they can also be ribonucleic acid sequences, or nucleic acid mimics, meaning compounds designed to preserve the hydrogen bonding and base-pairing properties of nucleic acid, but which differ from natural nucleic acid in, for example, susceptibility to nucleases.

reference protein or sequence

A reference protein sequence is AA64-300 of SEQ ID NO:4 or AA1-300 of SEQ ID NO:4 or a sequence differing therefrom by at least one of the residue differences found in SEQ ID NOS:5, 20, 22, or 24. A reference protein is a protein having the reference protein sequence. With reference to FIG. 5, examples of reference proteins are (a) a protein with sequence of AA64-300 of SEQ ID NO:4 except that residue 128 is serine or (b) a protein with sequence of SEQ ID NO:4 except that before $Leu^1$ is serine. In a preferred embodiment, the N-terminal additions from SEQ ID NOS:22 and 24 are $N_2$-Ala, $NH_2$-IleAla, $NH_2$-ArIleAla, $NH_2$-SerArgIleAla, $NH_2$-ArgSerArgIleAla, $NH_2$-GlyArgSerArgIleAla or $NH_2$-ProGlyArgSerArgIleAla sequence identity "Identity," as known in the art, is a relationship between two or more polypeptide sequences or two or more polynucleotide sequences, as determined by comparing the match between strings of such sequences. "Identity" is readily calculated by known methods (*Computational Molecular Biology,* Lesk. A. M. ed. Oxford University Press. New York. 1988: *Biocomputing: Informatics and Genome Projects,* Smith, D. W . ed., Academic Press, New York, 1993; *Computer Analysis of Sequence Data.* Part 1.

Griffin, A. M., and Griffin. H. G., eds., Humana Press, New Jersey, 1994; *Sequence Analysis in Molecular Biology,* von Heinje, G. Academic Press, 1987; and *Sequence Analysis Primer,* Gribskov, M. and Devereux. J., eds. M Stockton Press, New York, 1991). While there exist a number of methods to measure identity between two sequences, the term is well known to skilled artisans. Methods commonly employed to determine identity between sequences include, but are not limited to those disclosed in Carillo, H., and Lipman, D., SIAM *J. Applied Math.,* 48:1073 (1988) or, preferably, in Needleman and Wunsch, *J. Mol. Biol.,* 48: 443–445. 1970, wherein the parameters are as set in version 2 of DNASIS (Hitachi Software Engineering Co., San Bruno, Calif.). Computer programs for determining identity are publicly available. Computer program methods to determine identity between two sequences include, but are not limited to, GCG program package (Devereux, J., et al., *Nucleic Acids Research* 12(1): 387 (1984)), BLASTP, BLASTN, and FASTA (Atschul, S. F. et al., *J. Molec. Biol.* 215: 403–410 (1990)). The BLAST X program is publicly available from NCBI (blast@ncbi.nlm.nih.gov) and other sources (*BLAST Manual,* Altschul, S., et al. NCBI NLM NIH Bethesda. Md. 20894. Altschul, S., et al. *J. Mol. Biol.* 215: 403–410 (1990)).

substantial homology

At least about 60% sequence homology, for example 60% sequence identity.

The present invention provides DNA and corresponding amino acid sequences of a krill-derived enzymes such as proteinases, which can be multifunctional proteins. Crustaceans. including antarctic krill, are useful sources for the multifunctional protein of the invention. A protein having "multifunctional activity," is defined herein as including at least one of a chymotrypsin, trypsin, collagenase, elastase or exo peptidase activity, or asialo $GM_1$ ceramide binding activity. For purification of krill-derived multifunctional protein, see, for example, U.S. patent application Ser. No.08/600,273 (filed Feb. 8, 1996) now U.S. Pat. No. 6,040,155. deFaire et al., inventors, entitled "Multifunctional Enzyme."

The present invention provides nucleic acids (such as ribonucleic acids or deoxyribonucleic acids) and polypeptides and analogs thereof, including nucleic acids that bind to a multifunctional protein encoding nucleic acid, as well as pharmaceutical compositions, gene therapy and antibodies and antisera against the multifunctional protein. Some of the nucleic acids and polypeptides are naturally occurring variants (isoforms) whereas others are non-naturally occurring (engineered) variants.

1. Nucleic Acids

The nucleic acid embodiments of the invention are preferably deoxyribonucleic acids (DNAs), both single- and double-stranded, and most preferably double-stranded deoxyribonucleic acids. However, they can also be, without limitation, ribonucleic acids (RNAs), as well as hybrid RNA:DNA double-stranded molecules.

Nucleic acids encoding a multifunctional protein include all multifunctional protein-encoding nucleic acids, whether native or synthetic, RNA, DNA, or cDNA, that encode a multifunctional protein, or the complementary strand thereof, including but not limited to nucleic acid found in a multifunctional protein-expressing organism. For recombinant expression purposes, codon usage preferences for the organism in which such a nucleic acid is to be expressed are advantageously considered in designing a synthetic multifunctional protein-encoding nucleic acid.

The nucleic acid sequences of the invention can encode, for example, one of several isoforms of a krill-derived protein. SEQ ID NOS:4, 5, and 8 represent three isoforms that share about 88–89% identity with each other in overlapping amino acids. See, for example, FIG. 1 which compares the DNA sequence of the first isoform, SEQ ID NO:1, with the DNA sequence of the second isoform, SEQ ID NO:2, which share about 88% identical nucleotides. See also, for example, FIG. 3, which provides a comparison of the DNA sequence of the third isoform (SEQ ID NO:7) and the first isoform (SEQ ID NO: 1), which share about 89% identical nucleotides.

These isoforms all lack the initiation codon methionine. Further, two of these three isoforms contain a hydrophobic sequence which may function as a signal sequence, namely, LLLALVAAASA, which is amino acid residues 1–11 in the first isoform, SEQ ID NO:4, and PGRSRIALLLALVAATASA, which is amino acid residues 1–19 in the third isoform, SEQ ID NO:8. These two isoforms additionally contain a pro-protein segment. The pro-protein segment is the segment of the protein, other than the hydrophobic segment, that is present in the precursor protein but absent in the mature protein. Without being limited to a particular theory it is possible that at least a part of the pro-protein segment may still be attached to the mature protein. Further, it is believed that krill-derived multifunctional proteins may have two chains linked by a disulfide bond. For example, a cysteine in the pro-protein segment may participate in a disulfide bond in the mature protein.

In the first isoform, the pro-protein segment has the following sequence, which corresponds to amino acid residues 12–63 in the first isoform, SEQ ID NO:4: AEWRWQ-FRHPTVTPNPRAKNPFRVTKSSPVQP-PAVRGTKAVENCGPVAPRNK. The third isoform has a pro-protein segment with the following sequence, which corresponds to amino acid residues 20–71 in SEQ ID NO:8: SEWRWQFRHPTVTPNPRANNPFRPSKVAPVQPPAV-RGTKAVENCGPVAPKNK. The remaining amino acid sequences of these polypeptides (other than the hydrophobic segment and the pro-protein segment) represent the mature protein. See FIG. 2, which provides a comparison of the amino acid sequence of the first isoform and the second isoform, which share about 89% identical amino acids. Additionally, see FIG. 4 which provides a comparison of the amino acid sequences of all three isoforms.

Further embodiments of the invention include nucleic acid sequences that encode polypeptides that are preferably present in the protein. The following examples are derived from the pro-protein segment of SEQ ID NO;4, and are polypeptides that are preferably present in the mature protein. Without being limited to a particular theory, these polypeptides may form at least part of a first amino acid chain that is linked via a disulfide bond to a second amino acid chain, which can be, for example, the mature protein. For instance, in certain preferred embodiments, tie nucleic acid further encodes a polypeptide sequence such as AVENCGPVAPR (SEQ ID NO:11), AVENCGPVAPRNK (SEQ ID NO:12), GTKAVENCGPVAPR (SEQ ID NO:13), GTKAVENCGPVAPRNK (SEQ ID NO:14), SSPVQP-PAVRGTKAVENCGPVAPR (SEQ ID NO:15), SSPVQP-PAVRGTKAVENCGPVAPRNK (SEQ ID NO:16), or AVENCGPVA (SEQ ID NO:25), or a sequence differing therefrom as indicated in the corresponding sequence fragments of SEQ ID NOS:21 or 24. Without being limited to a particular theory, the above-listed polypeptides (SEQ ID NO:11–16, 25) may be linked to the remainder of the mature krill-derived multifunctional protein via a disulfide bond as follows. For example, the cysteine residue in one of these sequences (SEQ ID NO:11–16, 25) may participate in a disulfide bond with, for example, a cysteine in the mature protein, such as a cysteine corresponding the cysteine at residue 171 of SEQ ID NO:4. At least one of these sequences (SEQ ID NO:11–16), 25) are therefore present in preferred embodiments of the invention. See, for example, the amino acid sequences of several proteins, namely, Factor VII, thrombin, kallikrein, a Limulus pro-clotting enzyme from the Japanese horshoe horsehoe crab (*Tachypleus tridentatus*), plasmin, hepsin and Factor XII, aligned with the amino acid sequence of SEQ ID NO:4. All of the proteins aligned with the krill-derived multifunctional protein, except for tie Limulus protein and Hepsin, are involved in the human blood coagulation pathway.

Without being limited to any particular theory, it is believed that krill-derived multifunctional proteins include a larger N-terminus than that found in the first, second or the third isoform, SEQ ID NO:4, SEQ ID NO:5 or SEQ ID NO:8, respectively NOS:4, 5 or 8, 20, 22 or 24.

The nucleic acids of the invention can encode engineered multifunctional proteins based on forming chimeric polypeptides from the above isoforms, for example. The hydrophobic sequence or the pro-protein segment of one naturally occurring isoform can optionally be matched with the mature protein sequences of another naturally occurring isoform or isoforms. For example, the mature protein segment of SEQ ID NO:4 is amino acids 64–300. SEQ ID NO:5, for instance, is a partial sequence of the second isoform, which has a mature protein sequence of about 75% of the length of the mature protein segment of SEQ ID NO:4. Therefore. certain embodiments of the invention include a chimeric polypeptide in which the N-terminus of the polypeptide of SEQ ID NO:5 is linked to the remaining 25% of the length of the mature protein sequence found in SEQ ID NO:4, namely amino acids 64–116. In another embodiment of the invention, a hypothetical chimeric sequence includes the first 63 amino acids of the protein of SEQ ID NO:4 together with the amino acid sequence of SEQ ID NO:5. See SEQ ID NO:6, which is a composite of the proteins of SEQ ID NO:4 and SEQ ID NO:5. See, for example, FIG. 2, which aligns SEQ ID NO:4 with SEQ ID NO:5. The nucleic acid sequence corresponding to the amino acid sequence of SEQ ID NO:6 is provided in SEQ ID NO:3, which provides the first 344 nucleic acids of SEQ ID NO: 1 together with the nucleic acid sequence of SEQ ID NO:2.

Thus, the nucleic acids of the invention include nucleic acids that code for the mature protein, the protein including the pro-protein segment or the protein including the hydrophobic segment and the pro-protein segment, or portions thereof For example, the nucleic acid of the first isoform, SEQ ID NO:1, or the chimeric molecule, SEQ ID NO:3. are nucleic acids encoding the pro-protein, including the hydrophobic sequence and the pro-protein segment. The chimeric molecule, SEQ ID NO:3, represents the first 344 nucleotides of SEQ ID NO: 1, coding for the hydrophobic sequence and the pro-protein segment of the protein and the first 25% of the mature protein, together with the 599 nucleotides of SEQ ID NO:2, coding for the remaining 75% of the mature protein.

Further, for example, the N-terminus of SEQ ID NO:8 can be attached to the mature protein sequences of SEQ ID NO:5, thereby forming a chimeric polypeptide, shown in SEQ ID NO:10. The corresponding DNA sequence can be found in SEQ ID NO:9.

Alternatively, for example, amino acid sequences of several isoforms can be used to create an engineered polypeptide. For example, the chimeric polypeptide of SEQ ID NO:6 can be further modified by adding to the N-terminus of the protein the amino acid sequence PGRSRIA, which is amino acid residues 1–7 from the N-terminus of the third isoform, SEQ ID NO:10.

Without being bound to a particular theory. it is believed that there are at least about 45 isoforms, each having a different amino acid at the position corresponding to amino acid residue 68 of SEQ ID NO:4, including glutamine, methionine, lysine and asparagine. Such isoforms and other homologous polypeptides can be isolated using the techniques described under Section 5 below, entitled "Means for Identifying Polypeptides with Multifunctional Activity."

To construct engineered variants of multifunctional protein-encoding nucleic acids, the native sequences of any of the isoforms can be used as a starting point and modified to suit particular needs. For example, in certain embodiments, the nucleic acid sequence need not include the sequences encoding the 5' portion of the amino acid sequence that is absent in the mature protein, including amino acids 1–63 of SEQ ID NO:4 Thus, in certain embodiments of the invention, the encoded polypeptide is homologous to or has the sequence of the mature protein only, and not the segments corresponding to the N-terminal portions that are removed during cellular processing, namely, the hydrophobic sequence and the pro-protein segment.

Nonetheless, in preferred embodiments of the nucleic acids of the invention, the sequences encoding the N-terminal portion of the amino acid sequence that is absent in the mature protein, including amino acids 1–63 of SEQ ID NO:4, are included in the nucleic acid sequences.

The amino acid sequence forming a synthetic multifunctional protein preferably includes an enzymatically active segment of a krill-derived multifunctional protein, such as amino acids 64–300 of SEQ ID NO:4, particularly including the histidine at residue 104, the aspartic acid at residue 151 and the serine at residue 246, which are implicated in the catalytic mechanism of serine proteases. Thus, the protein need not include the hydrophobic sequence or pro-protein segment that are present in a krill-derived protein before cellular processing occurs, although the hydrophobic sequence and the pro-protein segment are preferably present.

Preferably, the nucleic acids will encode polypeptides having at least about 70% homology, more preferably, at least about 80% homology, even more preferably, at least about 85% homology, yet more preferably at least about 90% homology, and most preferably at least about 95% homology to a reference protein or a krill-derived multifunctional protein, such as the polypeptides of SEQ ID NO:4, SEQ ID NO:5, SEQ ID NO:6, SEQ ID NO:8 or SEQ ID NO:10, NOS:4, 5, 6, 8, 10, 20, 22 or 24 or amino acid sequences 64–300 of SEQ ID NO:4, or other naturally occurring isoforms. Even more preferably, the nucleic acids will encode polypeptides sharing at least about 70% identity, more preferably, at least about 80% identity, vet more preferably, at least about 85% identity, still more preferably at least about 90% identity, and most preferably at least about 95% identity with a krill-derived multifunctional protein.

Additionally, the invention includes a substantially pure nucleic acid comprising a nucleic acid that binds to a nucleic acid encoding a polypeptide having at least about 70% homology to a reference protein or a krill-derived multifunctional protein. Even more preferably, the nucleic acid binds to a nucleic acid encoding a polypeptide having at least about 80% homology, and more preferably, at least about 90% homology to a krill-derived multifunctional protein. Yet more preferably, the nucleic acid binds to a nucleic acid encoding a polypeptide sharing at least about 70% amino acid identity, and more preferably, at least about 80% amino acid identity, and yet more preferably, at least about 90% amino acid identity, with a krill-derived multifunctional protein, such as the polypeptide of SEQ ID NO:4, SEQ ID NO:5, SEQ ID NO:6, SEQ ID NO:8 or SEQ ID NO:10 and especially, SEQ ID NO:4, SEQ ID NO:6 or SEQ ID NO:10. A nucleic acid that binds to a nucleic acid that encodes a polypeptide homologous to a krill-derived multifunction protein can be used as a probe, for example, to identify additional multifunctional proteins or to determine multifunctional protein expression.

Numerous methods for determining percent homology (such as similarity or identity) are known in the art. One preferred method is to use version 6.0 of the GAP computer program for making sequence comparisons. The program is available from the University of Wisconsin Genetics Computer Group and utilizes the alignment method of Needleman and Wunsch. *J. Mol. Biol.* 48, 443. 1970, as revised by Smith and Waterman *Adv. Appl. Math.* 2, 482, 1981. Numerous methods for determining percent identity are also known in the art, and a preferred method is to use the FASTA computer program, which is also available from the University of Wisconsin Genetics Computer Group.

The mature protein of the polypeptide of SEQ ID NO:4 is about 61% identical to the chymotrypsin-like serine proteinase in the shrimp *Penaeus vannamei* according to the sequence provided by Genbank (Mountain View, Calif.), database acquisition no. X66415, and about 60% identical to the collagenolytic serine proteinase in the fiddler crab *Uca pugilator*, according to the sequence provided by Genbank, database acquisition no. U49931. The amino acid sequence of the pro-protein of SEQ ID NO:4 is about 53% identical to the precursor of the chymotrypsin-like serine proteinase in the shrimp *Penaeus vannamei*, and about 51% identical to the precursor of the collagenolytic serine proteinase in the fiddler crab *Uca pugilator*. Preferably, the nucleic acids encoding polypeptides having multifunctional activity are less than about 70% identical to the above-identified proteinases of *Penaeus vannamei* or *Uca pugilator*.

In addition to nucleic acids encoding a multifunctional protein, the present invention includes nucleic acids encoding polypeptides that are homologous to a reference protein or a krill-derived multifunctional protein or that share a percentage identity with a reference protein or a krill-derived multifunctional protein. Further, the present invention includes nucleic acids that encode a portion of a multifunctional protein or a variant thereof, such as the enzymatically active portion of the protein or the portion of the protein that provides asialo $GM_1$ ceramide binding activity.

The invention also is directed to a nucleic acid encoding a krill-derived multifunctional protein that has at least one of the following activities: chymotrypsin, trypsin, collagenase, elastase and exopeptidase activity or asialo $GM_1$ ceramide binding activity. Preferably, the encoded polypeptide will be effective to remove or inactivate a cell-surface adhesion molecule, and most preferably, the encoded polypeptide will be pharmaceutically effective.

For identifying the active segment or segments of multifunctional protein, one approach is to take a multifunctional protein cDNA and create deletional mutants lacking segments at either the 5' or the 3' end by, for instance, partial digestion with S1 nuclease, Bal 31 or Mung Bean nuclease (the latter approach described in literature available from Stratagene, San Diego, Calif. in connection with a commercial deletion cloning kit). Alternatively, the deletion mutants are constructed by subcloning restriction fragments of a multifunctional protein cDNA. The deletional constructs are cloned into expression vectors and tested for their multifunctional activity.

These structural genes can be altered by mutagenesis methods such as that described by Adelman et al., *DNA*, 2: 183. 1983 or through the use of synthetic nucleic acid strands. The products of mutant genes can be readily tested for multifunctional activity.

The nucleic acid sequences can be further mutated, for example, to incorporate useful restriction sites. See Maniatis et al. *Molecular Cloning, a Laboratory Manual* (Cold Spring Harbor Press, 1989). Such restriction sites can be used to create "cassettes", or regions of nucleic acid sequence that are facilely substituted using restriction enzymes and ligation reactions. The cassettes can be used to substitute synthetic sequences encoding mutated multifunctional protein amino acid sequences.

The multifunctional protein-encoding sequence can be, for instance, substantially or fully synthetic. See, for example, Goeddel et al., *Proc. Natl. Acad. Sci. USA*, 76, 106–110, 1979. For recombinant expression purposes, codon usage preferences for the organism in which such a nucleic acid is to be expressed are advantageously considered in designing a synthetic multifunctional protein-encoding nucleic acid. Since the nucleic acid code is degenerate, numerous nucleic acid sequences can be used to create the same amino acid sequence.

Further, with an altered amino acid sequence, numerous methods are known to delete sequence from or mutate nucleic acid sequences that encode a polypeptide and to confirm the function of the polypeptides encoded by these deleted or mutated sequences. Accordingly, the invention also relates to a mutated or deleted version of a multifunctional protein nucleic acid that encodes a polypeptide that retains multifunctional protein activity.

Conservative mutations of the naturally occurring isoforms are preferred for engineered variants. Such conservative mutations include mutations that switch one amino acid for another within one of the following groups:
1. Small aliphatic, nonpolar or slightly polar residues: Ala. Ser, Thr, Pro and Gly;
2. Polar, negatively charged residues and their amides: Asp, Asn, Glu and Gln;
3 Polar, positively charged residues: His, Arg and Lys;
4. Large aliphatic. nonpolar residues: Met, Leu, Ile, Val and Cys; and
5 Aromatic residues: Phe, Tyr and Trp.

A preferred listing of conservative substitutions is the following:

| Original Residue | Substitution |
| --- | --- |
| Ala | Gly, Ser |
| Arg | Lys |
| Asn | Gln, His |
| Asp | Glu |
| Cys | Ser |
| Gln | Asn |
| Glu | Asp |
| Gly | Ala, Pro |
| His | Asn, Gln |
| Ile | Leu, Val |
| Leu | Ile, Val |
| Lys | Arg, Gln, Glu |

-continued

| Original Residue | Substitution |
|---|---|
| Met | Leu, Tyr, Ile |
| Phe | Met, Leu, Tyr |
| Ser | Thr |
| Thr | Ser |
| Trp | Tyr |
| Tyr | Trp, Phe |
| Val | Ile, Leu |

The types of substitutions selected may be based on the analysis of the frequencies of amino acid substitutions between homologous proteins of different species developed by Schulz et al., *Principles of Protein Structure,* Springer-Verlag, 1978, pp. 14–16, on the analyses of structure-forming potentials developed by Chou and Fasman, *Biochemistry* 13, 211, 1974 or other such methods reviewed by Schulz et al. *Principles in Protein Structure,* Springer-Verlag. 1978, pp. 108–130, and on the analysis of hydrophobicity patterns in proteins developed by Kyte and Doolittle, *J. Mol. Biol.* 157: 105–132, 1982.

2. Polypeptides

Polypeptides of the invention include all polypeptides having multifunctional activity. whether native or synthetic, including but not limited to polypeptides purified from a multifunctional protein-expressing organism. A preferred embodiment of the invention provides a polypeptide comprising a substantially pure isoform of a reference protein or a krill-derived multifunctional protein or engineered variant thereof, and more preferably, a polypeptide comprising SEQ ID NO:4, SEQ ID NO:5, SEQ ID NO:6, SEQ ID NO:8 or SEQ ID NO:10 NOS:4, 5, 6, 8, 10, 20, 22 or 24 and especially, SEQ ID NO:4, SEQ ID NO:6 or SEQ ID NO:10 NOS:4, 6 10 or 22 Further, polypeptides of the invention preferably comprise at least one of the amino acid sequences of SEQ ID NO NOS: 11–16 and 25.

In addition to the a reference protein or a multifunctional protein, and its their isoforms and portions thereof the present invention includes polypeptides that are homologous to a reference protein or a krill-derived multifunctional protein or that share a percentage identity with a reference protein or a krill-derived multifunctional protein. Further, the present invention includes portions of the a reference protein or a multifunctional protein or a variant thereof, such as the enzymatically active portion of the protein or the portion of the protein that provides asialo GM$_1$ ceramide binding activity.

Additionally, the present invention includes engineered variants of multifunctional proteins that retain multifunctional activity. In certain embodiments, these engineered variants lack, for example, no more than about 63 amino acid residues at the N-terminal end of SEQ ID NO:4.

Preferably, the variants will have at least about 70% homology, more preferably, at least about 80% homology, even more preferably, at least about 85% homology, still more preferably at least about 90% homology, and most preferably at least about 95% homology to a krill-derived multifunctional protein, such as the polypeptides of SEQ ID NO:4, SEQ ID NO:5, SEQ ID NO:6, SEQ ID NO:8, SEQ ID NO:10, or other isoforms, or amino acid sequences 64–300 of SEQ ID NO:4. Even more preferably, the analogs will share at least about 70% identity, more preferably at least about 80% identity, yet more preferably, at least about 85% identity, still more preferably at least about 90% identity, and most preferably at least about 95% identity with a krill-derived multifunctional protein. Preferably, the polypeptide has the sequence of a contiguous stretch of at least about 237 amino acids of the following mature proteins: in SEQ ID NO:4, amino acid residues 64–300: in SEQ ID NO:6, amino acid residues 64–300; and in SEQ ID NO:10, amino acid residues 72–308.

Amino acid analogs of the above-described polypeptides are also included in the present invention.

Additionally, the present invention provides a pharmaceutical composition for treating an animal comprising an effective amount of a polypeptide comprising a substantially pure isoform of a krill-derived multifunctional protein or engineered variant thereof and a pharmaceutically acceptable carrier. More preferably, the polypeptide comprises SEQ ID NO:4, SEQ ID NO:5, SEQ ID NO:6, SEQ ID NO:8 or SEQ ID NO:10, and even more preferably, SEQ ID NO:4, SEQ ID NO:6 or SEQ ID NO:10, and the polypeptide preferably comprises at least one of the amino acid sequences of SEQ ID NO:11–16.

3. Methods of Synthesizing Polypeptides

In one embodiment, the polypeptides of the invention are made as follows, using a gene fusion. For example, fusion to maltose-binding protein ("MBP") can be used to facilitate the expression and purification of a multifunctional protein in a prokaryote such as *E coli.* The hybrid protein can be purified, for example, using affinity chromatography using the binding protein's substrate. See, for example, *Gene* 67: 21–30 (1988). When using a fusion protein that includes maltose binding protein, a cross-linked amylose affinity chromatography column can be used to purify the protein.

The cDNA specific for a given multifunctional protein or analog thereof can also be linked using standard means to a cDNA for glutathione s-transferase ("GST"), found on a commercial vector, for example. The fusion protein expressed by such a vector construct includes the multifunctional protein or analog and GST, and can be treated for purification.

Should the MBP or GST portion of the fusion protein interfere with function, it is removed by partial proteolytic digestion approaches that preferentially attack unstructured regions. such as the linkers between MBP or GST and the multifunctional protein. The linkers are designed to lack structure, for instance using the rules for secondary structure-forming potential developed by Chou and Fasman, *Biochemistry* 13, 211, 1974. The linker is also designed to incorporate protease target amino acids, such as trypsin, arginine and lysine residues. To create the linkers, standard synthetic approaches for making oligonucleotides are employed together with standard subcloning methodologies. Other fusion partners other than GST or MBP can also be used.

Additionally, the multifunctional proteins can be directly synthesized from nucleic acid (by the cellular machinery) without use of fusion partners. For instance, nucleic acids having the sequence of SEQ ID NO:1, SEQ ID NO:3 or SEQ ID NO:9 are subcloned into an appropriate expression vector having an appropriate promoter and expressed in an appropriate organism. Antibodies against the krill multifunctional protein can be employed to facilitate purification.

Additional purifications techniques are applied as needed, including without limitation, preparative electrophoresis, FPLC (Pharmacia, Uppsala, Sweden), HPLC (e.g., using gel filtration, reverse-phase or mildly hydrophobic columns), gel filtration, differential precipitation (for instance, "salting out" precipitations), ion-exchange chromatography and affinity chromatography (including affinity chromatography using the RE1 duplex nucleotide sequence as the affinity ligand).

A polypeptide or nucleic acid is "isolated" in accordance with the invention in that the molecular cloning of the nucleic acid of interest, for example, involves taking a multifunctional protein nucleic acid from a cell, and isolating it from other nucleic acids. This isolated nucleic acid may then be inserted into a host cell, which may be yeast or bacteria, for example. A polypeptide or nucleic acid is "substantially pure" in accordance with the invention if it is predominantly free of other polypeptides or nucleic acids, respectively. A macromolecule, such as a nucleic acid or a polypeptide, is predominantly free of other polypeptides or nucleic acids if it constitutes at least about 50% by weight of the given macromolecule in a composition. Preferably, the polypeptide or nucleic acid of the present invention constitutes at least about 60% by weight of the total polypeptides or nucleic acids, respectively, that are present in a given composition thereof, more preferably about 80%, still more preferably about 90%, yet more preferably about 95%, and most preferably about 100%. Such compositions are referred to herein as being polypeptides or nucleic acids that are 60% pure, 80% pure, 90% pure, 95% pure, or 100% pure, any of which are substantially pure.

4. Preferred Characteristics of the Multifunctional Protein

Krill, including without limitation krill of the genuses Euphasia (such as *superba, crystallorphias, frigida, triacantha, vellantini, lougirostris, lucens, similis, spinifera, recurva* and the like), Meganyctiphanes (such as *norvegica* and the like) and Tysanoessa (such as *macurura, vicina, gregaria* and the like), are a preferred source of krill-derived multifunctional proteins.

Preferably, the protein has a molecular weight between about 20 kd and about 40 kd, and more preferably from about 26 kd to about 32 kd, and most preferably about 29 kd, as determined by sodium dodecyl sulfate ("SDS") polyacrylamide gel electrophoresis ("PAGE"). Further, the protein preferably has substantial homology to a krill-derived multifunctional protein. Preferred proteins are hydrolases, and preferably, proteases. Preferably, the protein is selectively reactive with cell-surface receptors such as polypeptides or glycolipids.

Protease activity can be determined by incubating a protein preparation with casein (concentration 1% w/v) at 30 C. for 20 hours and measuring the release of amino acids or peptides (which can be measured by the increase in colorometrically determinable amino groups). Isolated multifunctional protein of 95% purity will typically have a specific activity of at least about 25 Casein Units per mg. Casein Units are defined in *Biochem. J.*, 173: 291–298, 1978 (using azocasein as the substrate).

Alternatively, tryptic protease activity can be measured against tyrosine-arginine-methyl-ester ("TAME"). The multifunctional protein (of at least about 95% purity) will preferably have specific activity of at least about 60 TAME Units per mg. Or, tryptic activity can be measured using Benzoyl-Val-Gly-Arg-p-$NO_2$-anilide as the substrate. Using this substrate and the method of *Biochemical J.* 185: 423–433, 1980, the multifunctional protein will preferably have specific activity of at least about 210 Units per mg. Chymotryptic activity can be measured using Succinyl-Ala-Ala-Pro-Phe-p-$NO_2$-anilide as the substrate. Using this substrate and the method of *J. Biol. Chem.*, 269: 19565–19572, 1994, the multifunctional protein will preferably have specific activity at least about 260 Units per mg. Elastase activity can be measured using Boc-Ala-Ala-Pro-Ala-p-$NO_2$-anilide as the substrate. Using this substrate and the method of *J. Biol. Chem.*, 269: 19565–19572, 1994, the multifunctional protein will preferably have specific activity of at least about 270 Units per mg.

Generally, the multifunctional protein will be sufficiently stable so that at least about 50% of the proteolytic activity is retained after incubation at 50° C. for 24 hours at pH 7.0 at a concentration of 5 mg/mi. Preferably at least about 50% of the proteolytic activity is retained after incubation at 60° C. for 5 hours at pH 7.0 at a concentration of 5 mg/mi.

Preferably, the pH optimum of the multifunctional protein is substrate dependent. For the substrate azocasein, the pH optimum is preferably from about 3.5 to about 6.5, more preferably, from about 4.0 to about 6.0. For the substrate Benzoyl-Val-Gly-Arg-p-nitroanilide, the pH optimum is preferably in excess of about 8.0, more preferably in excess of about 9.0. For the substrate Boc-Ala-Ala-Pro-Ala-p-nitroanilide, the pH optimum is preferably between about 6.0 and about 7.0, more preferably about 7.0.

Using Benzoyl-Val-Gly-Arg-p-nitroanilide as the substrate, the $K_m$ at about pH 9.5 in the presence of 2 mM $Ca^{2+}$ is preferably between about 200 and about 240 $\mu$M. Using Succinyl-Ala-Ala-Pro-Phe-p-nitroanilide as the substrate, the $K_m$ at pH 9.5 in the presence of 2 mM $Ca^{2+}$ is preferably between about 250 and about 290 $\mu$M.

Preferably, the multifunctional protein has a temperature optimum for activity against casein of between about 45° C. and about 60° C. Generally, the protein retains at least about 50% of its activity when incubated at 5 mg/ml for 18 hours at a pH ranging from about 5.0 to about 9.5 at25 C.

When HL60 cells are pretreated with krill-derived multifunctional hydrolase, their binding to TNF stimulated endothelial cells is inhibited by more than about 60%. Preferably, treatment of HL60 or endothelial cells with the multifunctional protein of the invention will inhibit HL60 cell binding to TNF stimulated endothelial cells by at least about 20%, more preferably at least about 40%, still more preferably at least about 60%, yet more preferably at least about 80%. Alternately, the multifunctional protein will preferably have at least about 30% of the adhesion-inhibiting activity of the krill-derived multifunctional hydrolase. More preferably, the multifunctional protein shall have at least about 60% of the adhesion inhibiting activity of the krill-derived multifunctional hydrolase, still more preferably at least about 80%, yet more preferably at least about 100%.

The multifunctional protein of the invention effectively removes or inactivates certain cell-surface adhesion molecules, such as ICAM-1 (i.e., CD 54). ICAM-2, VCAM-1, CD4, CD8, CD28, CD31, CD44 and the asialo $GM_1$ ceramide, without affecting cell viability. This adhesion site removal or inactivation phenomenon is believed to provide at least a partial explanation for the protein's effectiveness against many, though probably not all, of the indications against which the multifunctional protein is effective as a treatment or preventative agent. Other cell surface receptors have been found to be substantially resistant to removal or inactivation by the multifunctional protein, such as the T-cell receptor, the Class I major histocompatibility complex or the integrins CD11and CD18.

5. Means for Identifying Polypeptides with Multifunctional Activity

In one aspect, the present invention provides methods for identifying polypeptides that are homologous to the multifunctional protein. Such polypeptides may be found, for example, in fish and crustaceans.

The method by which multifunctional protein cDNA was isolated illustrates how readily multifunctional proteins are identified. For instance, see Example 1. The same methodology can be used to identify other sequences from other sources that have multifunctional activity.

Additionally, probes for multifunctional protein expression can be used, for example, to detect the presence of a multifunctional protein. Such probes include antibodies directed against multifunctional protein or fragments thereof, nucleic acid probes that hybridize to multifunctional protein mRNA under stringent conditions, and oligonucleotides that specifically prime a PCR amplification of multifunctional protein mRNA. Nucleic acid molecules that bind to a multifunctional protein-encoding nucleic acid under high stringency conditions are identified functionally, or by using the hybridization rules reviewed in Sambrook et al., *Molecular Cloning: A Laboratory Manual,* 2nd ed., Cold Spring Harbor Press, 1989.

Many deletional or mutational analogs of nucleic acid sequences for a multifunctional protein are effective hybridization probes for multifunctional protein-encoding nucleic acid. Accordingly the present invention relates to nucleic acids that hybridize with such multifunctional protein-encoding nucleic acids under stringent conditions. Preferably, the nucleic acid of the present invention hybridizes with at least a segment of the nucleic acid described as SEQ ID NO:1, SEQ ID NO:2, SEQ ID NO:3, SEQ ID NO:7 or SEQ ID NO:9 NOS: 1, 2, 3, 7, 9, 19, 21 or 23 under stringent conditions.

"Stringent conditions" refers to conditions that allow for the hybridization of substantially related nucleic acids, where relatedness is a function of the sequence of nucleotides in the respective nucleic acids. For instance, for a nucleic acid of 100 nucleotides, such conditions will generally allow hybridization thereto of a second nucleic acid having at least about 85% homology, and more preferably having at least about 90% homology. Such hybridization conditions are described by Sambrook et al., *Molecular Cloning: A Laboratory Manual,* 2nd ed., Cold Spring Harbor Press, 1989.

PCR (polymerase chain reaction) can be used to detect nucleic acids having multifunctional protein sequences through amplification of such sequences using multifunctional protein nucleic acid primers. PCR methods of amplifying nucleic acids utilize at least two primers one primer and often at least two. One of these primers is capable of hybridizing to a first strand of the nucleic acid to be amplified and of priming protein-driven nucleic acid synthesis in a first direction. The other is capable of hybridizing the reciprocal sequence of the first strand (if the sequence to be amplified is single stranded, this sequence is initially hypothetical, but is synthesized in the first amplification cycle) and of priming nucleic acid synthesis from that strand in the direction opposite the first direction and towards the site of hybridization for the first primer. Conditions for conducting such amplifications, particularly under preferred high stringency conditions, are well known. See. for example, *PCR Protocols,* Cold Spring Harbor Press, 1991.

Antibodies against multifunctional proteins can also be used to identify polypeptides that are homologous to multifunctional protein. Antigens for eliciting the production of antibodies against the a reference protein or a multifunctional protein can be produced recombinantly by expressing all of or a part of the nucleic acid of a reference protein or a multifunctional protein in a prokaryote such as bacteria or a eukaryote such as yeast. In one embodiment, the recombinant protein is expressed as a fusion protein, with the non-multifunctional functional protein portion of the protein serving either to facilitate purification or to enhance the immunogenicity of the fusion protein. For instance, the non-multifunctional functional protein portion comprises a protein for which there is a readily-available binding partner that is utilized for affinity purification of the fusion protein. The antigen includes an "antigenic determinant," i.e., a minimum portion of amino acids sufficient to bind specifically with an anti-multifunctional protein antibody.

Antisera to a reference protein or a reference protein or a multifunctional protein can be made, for example, by creating a multifunctional protein antigen by linking a portion of the cDNA for human multifunctional protein to a cDNA for glutathione s-transferase ("GST") found on a commercial vector. The resulting vector expresses a fusion protein containing an antigenic segment of multifunctional protein and GST that is readily purified from the expressing bacteria using a glutathione affinity column. The purified antigenic fusion protein is used to immunize rabbits. The same approach is used to make antigens based on other segments of the multifunctional protein. Procedures for making antibodies and for identifying antigenic segments of proteins are well known. See, for instance, Harlow, Antibodies, Cold Spring Harbor Press, 1989.

6. Gene Therapy

The invention also encompasses the use of gene therapy approaches to insert a gene expressing a multifunctional protein or a polypeptide with multifunctional protein activity. For gene therapy, medical workers prefer to incorporate, into one or more cell types of an organism, a DNA vector capable of directing the synthesis of a polypeptide missing from the cell or useful to the cell or organism when expressed in greater amounts. The methods for introducing DNA to cause a cell to produce a new polypeptide or a greater amount of a polypeptide are called "transfection" methods. See, generally, Sambrook et al., *Molecular Cloning: A Laboratory Manual,* 2nd ed., Cold Spring Harbor Press, 1989.

For viral gene therapy vectors, dosages are generally from about 1 g to about 1 mg of nucleic acid per kg of body mass. For non-infective gene therapy vectors, dosages are generally from about 1 g to about 100 mg of nucleic acid per kg of body mass.

7. Routes of Administration

The multifunctional protein polypeptides and nucleic acid compositions of the invention can be administered orally, topically, rectally, vaginally, by instillation (for instance into the urinary tract or into fistulas), by pulmonary route by use of an aerosol, by application of drops to the eye, or systemically, such as parenterally, including, for example, intramuscularly, subcutaneously, intraperitoneally intraarterially or intravenously. The multifunctional protein composition can be administered alone, or it can be combined with a pharmaceutically-acceptable carrier or excipient according to standard pharmaceutical practice. For the oral mode of administration, the multifunctional protein composition can be used in the form of tablets, capsules, lozenges, chewing gum, troches, powders, syrups, elixirs, aqueous solutions and suspensions, and the like. In the case of tablets, carriers that is used include lactose, sodium citrate and salts of phosphoric acid. Various disintegrants such as starch, and lubricating agents such as magnesium stearate and talc, are commonly used in tablets. For oral administration in capsule form, useful diluents are lactose and high molecular weight polyethylene glycols. If desired, certain sweetening and/or flavoring agents are added. For parenteral administration, sterile solutions of the multifunctional protein are usually prepared, and the pHs of the solutions are suitably adjusted and buffered. For intravenous use, the total concentration of solutes should be controlled to render the preparation isotonic. For ocular administration, ointments or droppable liquids may be delivered by ocular delivery systems known to the art such as applicators or eye droppers. Such compositions can include mucomimetics such as hyaluronic acid, chondroitin sulfate, hydroxypropyl methylcellulose or polyvinyl alcohol, preservatives such as sorbic acid, EDTA or benzylchronium chloride, and the usual quantities of diluents and/or carriers. For pulmonary administration, diluents and/or carriers will be selected to be appropriate to allow the formation of an aerosol. For topical administrations, the multifunctional protein is typically administered in aqueous form or in a hydrogel. A preferred hydrogel comprises an aqueous suspension of from about 1% (w/v) to about 10% of low molecular weight hydrolyzed starch.

Suppository forms of the multifunctional protein are useful for vaginal, urethral and rectal administrations. Such suppositories will generally be constructed of a mixture of substances that is solid at room temperature but melts at body temperature. The substances commonly used to create such vehicles include theobroma oil, glycerinated gelatin, hydrogenated vegetable oils, mixtures of polyethylene glycols of various molecular weighty and fatty acid esters of polyethylene glycol. See, Remington's Pharmaceutical Sciences, 16th Ed., Mack Publishing, Easton. Pa. 1980. pp. 1530–1533 for further discussion of suppository dosage forms. Analogous gels or cremes can be used for vaginal, urethral and rectal administrations.

Numerous administration vehicles will be apparent to those of ordinary skill in the art. including without limitation slow release formulations, liposomal formulations and polymeric matrices.

For topical treatments, a suitable dose of multifunctional protein per application ranges from about 0.1 $\mu g/cm^2$ to about 1 $mg/cm^2$, preferably from about 1 $\mu g/cm^2$ (for example, using about 10 $\mu g/ml$) to about 1 $mg/cm^2$ (for example, using about 10 mg/ml), more preferably from about 5 $\mu g/cm^2$ (for example, using about 50 $\mu g/ml$) to about 100 $\mu g/cm^2$ (for example, using about 1 mg/ml), yet more preferably from about 10 $1\mu g/cm^2$ to about 250 $\mu g/cm^2$, still yet more preferably from about 10 $\mu g/cm^2$ (for example, using about 100 $\mu g/ml$) to about 50 $\mu g/cm^2$ (for example, about 500 $\mu g/ml$). For systemic treatments, dosages will generally be selected to maintain a serum level of multifunctional protein between about 0.1 $\mu g/100$ cc and about 5 $\mu g/100$ cc, preferably between about 0.5 $\mu g/100$ cc and about 2.0 $\mu g/100$ cc. In an alternative measure of preferred systemic administration amounts, preferably from about 0.1 mg/kg to about 10 mg/kg, more preferably about 1 mg/kg, will be administered (although toxicology in animal models suggests that in excess of 25 mg/kg is acceptable). For ocular treatments, a suitable dose of multifunctional protein per application ranges from about 0.01 mg per eve to about 5 mg per eye, preferably from about 0.1 mg per eve to about 2.0 mg per eye. For vaginal and urinary tract treatments, suitable flushing/instillation solutions of the multifunctional protein will generally have concentrations from about 1 $\mu g/ml$ to about 15 mg/ml, preferably from about 100 $\mu g/ml$ to about 3 mg/ml. For oral treatments, suitable mouthwash solutions will generally have concentration of multifunctional protein from about 1 mg/ml to about 15 mg/ml preferably from about 2 mg/ml to about 10 mg/ml. Lozenges will typically contain from about 100 $\mu g$ to about 10 mg of multifunctional protein. Aerosols will generally be made from solutions having protein concentrations from about 0.1 mg/ml to about 15 mg/ml, preferably from about 1 mg/ml to about 10 mg/ml. Generally, from about 0.1 ml to about 2 ml of aerosol will be applied to the airways of the patient, preferably from about 0.5 ml to about 1.0 ml. For scar and keloid treatments, generally between about 0.1 mg and about 5 mg of multifunctional protein will be injected into each $cm^2$ of the lesion, preferably from about 0.5 mg to about 3 mg. For treating adhered connective tissue or joints, generally between about 0.5 mg and about 10 mg of multifunctional protein will be injected interstitially at the adhesion, preferably between about 1 mg and about 5 mg. For all treatments, the protein composition will generally be applied from about 1 to about 10 times per day, preferably from about 2 to about 5 times per day. These values, of course, will vary with a number of factors including the type and severity of the disease, and the age, weight and medical condition of the patient, as will be recognized by those of ordinary skill in the medical arts. It is believed that substantially higher doses can be used without substantial adverse effect.

For treating or preventing infection, the multifunctional protein can be administered systemically or in a manner adapted to target the affected tissue. For preventing cold or influenza transmission, the composition is preferably applied to the lungs or airways. For treating immune disorders, the composition may be applied systemically or in a manner adapted to target the affected tissue. For treating the primary and secondary infections of leprosy, the primary administration route will generally be the topical route. For treating scar or keloid tissue, generally the composition will be injected into the scar or keloid, except that for corneal scars the composition will generally be applied ocularly without injection. For cancer treatment, the composition will generally be administered systemically by a route or in a manner adopted to target the affected tissue. For treating atherosclerosis, the composition will generally be administered systemically, although the site of administration may be chosen to administer the highest dosages to the portion of the circulatory system most at risk. For asthma, the general route of administration will be pulmonary. For treating pseudomonas infections, the infection will typically be a lung infection and the administration route pulmonary. For reperfusion injury, the composition will generally be administered systemically, although the site of administration may be designed to administer the highest dosages to the portion of the body that suffered an ischemic event. For treating the painful symptoms of malaria, the administration mode will generally by systemic.

For wound healing, the multifunctional protein is preferably be applied more often than simply the time at which the wound is first dressed. Preferably, the multifunctional protein is applied at least about every time the wound dressing is changed. The multifunctional protein can also be applied at least about every other day, more preferably, every day. In one embodiment, the multifunctional protein is administered to a wound substantially free of necrotic tissue. The phrase "substantially free of necrotic tissue" shall mean sufficiently lacking in necrotic tissue so that an ordinarily-skilled pathologist would consider any residue of necrotic tissue to be irrelevant to determining a wound-healing prognosis.

For organ transplants, the organ to be transplanted will preferably be bathed in a solution of the multifunctional protein for between about 10 minutes and about 5 hours. The protein solution will preferably contain between about 0.01 mg/ml and about 25 mg/ml of the multifunctional protein, more preferably, between about 0.5 mg/ml and about 5 mg/ml. After transplantation, the multifunctional protein will preferably be administered systemically using the conditions described above.

For cleaning contact lenses in situ the solutions described above for ocular treatments are preferred; For ex vivo treatments, higher concentrations of protein will generally be used. Cleaning incubations of from about 5 to about 30 minutes at from about 20° C. to about 50° C. are also preferred. For ex vivo treatments, the higher end of the temperature range is preferred.

For leprosy, many of the associated infections will be appropriately treated with a topical application of the multifunctional protein. For CF or COPD, the multifunctional protein can be used to treat (a) the build up of viscous fluids in the lungs and (b) associated pulmonary infections. Preferably, treatments of CF and COPD patients include pulmonary treatments with an aerosol of the multifunctional protein, but can include other routes of administration including systemic administrations.

Particularly important among the diseases relevant to the transmission inhibitory embodiment of the invention are sexually-transmitted diseases, such as candida, gonorrhea, chlamydia, syphilis, trichomonas, chancroid, HIV, herpes or hepatitis infections. Among these, viral diseases are particularly preferred targets for transmission prevention; HIV is a still more preferred target. For this use, the body cavity involved in sexual activity is generally rinsed or flushed with a composition containing the multifunctional protein, or a creme, gel or suppository designed to localize the composition to the body cavity is used. The composition can be used soon before, in conjunction with, or soon after, sexual activity, although prior or concurrent use is preferred.

For herpes infections, the viral targets include HSV-1, which primarily manifests as oral herpes, HSV-2, which primarily manifests as genital herpes, and herpes zoster.

For autoimmune diseases or diseases with autoimmune components, treatment targets include without limitation rheumatoid arthritis, multiple sclerosis, primary biliary cirrhosis, active chronic hepatitis, ulcerative colitis, rheumatic arthritis, scleroderma, systemic lupus erythematosus, Hashimoto's thyroiditis, primary myxedema, thyroroxicosis, pernicious anemia. Addison's disease, premature onset of menopause, autoimmune male infertility, insulin-dependent diabetes, type B insulin resistance of acanthosis nigricans, alopic allergy, myasthenia gravis, Lambert-Eaton syndrome. Goodpasture's syndrome, pemphigus vulgaris, pemphigoid, phacogenic uveitis, sympathetic ophthalmia, autoimmune hemolytic anemia, idiopathic thrombocytopenic purpura, Sjogren's syndrome, discoid lupus erythematosus, dermatomyositis and mixed connective tissue disease.

For adhesion disorders, the cells or viruses involved can include, without limitation, endothelial cells, lymphocytes, including T-cells, tumor cells, microbial cells, viruses, including HIV and herpes. Adhesion processes are believed to be involved in tissue invasion, for instance, by immune cells, microbes, and tumor cells.

For many of diseases for which the multifunctional protein of the invention is useful as a prophylactic treatment, including those not caused by microbes, a patient's medical history, lifestyle or genetic background will often indicate a predisposition to acquire the disease. This is true, for instance, of atherosclerosis.

Generally, the multifunctional protein will be administered in an effective amount. An effective amount is an amount effective to either (1) reduce the symptoms of the disease sought to be treated, (2) induce a pharmacological change relevant to treating the disease sought to be treated, (3) inhibit or prevent infection or re-infection by an infective agent, or (4) prevent the occurrence of a non-infectious disease (for instance a disease treatable by blocking a cell adhesion phenomenon). For cancer, an effective amount further includes an amount effective to: prevent or limit metastasis, for instance, to reduce the level of metastasis: reduce the size of a tumor, slow the growth of a tumor; and increase the life expectancy of the affected animal. For wound treatment, in one aspect, an effective amount includes an amount which, if regularly applied, prevents the occurrence of infection. In another aspect, for wound healing, an effective amount includes an amount effective to reduce the average time it takes for a wound to heal.

Humans are the preferred subjects for treatment. However, the multifunctional protein can be used in many veterinary contexts to treat animals, preferably to treat mammals, as will be recognized by those of ordinary skill in light of the present disclosure.

The present invention is further exemplified by the following non-limiting examples.

EXAMPLE 1

Cloning of PHIM Polypeptide

The PHIM polypeptide was purified and the polypeptide was partially sequenced, as described in U.S. patent application Ser. No. 08/600,273 (filed Feb. 8, 1996), now U.S. Pat. No. 6,040,155, deFaire et al., inventors, entitled "Multifunctional Enzyme." Degenerate oligonucleotide primers were constructed based on the partial amino acid sequence. The primers had the following sequences: CACGCCTAC-CCITGGCA (SEQ ID NO:17) and GTGTTGGACTC-GATCCAGATC (SEQ ID NO: 18). The primers were used to screen a krill cDNA library that was constructed in lambda zap, using the lambda zap cDNA synthesis kit (Stratagene. San Diego, Calif.). Three positive clones were identified through screening with a PCR fragment as a probe. The PCR fragment used as a probe was sequences 217 to 881 of SEQ ID NO:1, with the following changes: at 219, T to C; at 222, T to C; at 228, C to G; at 270, T to A; at 330,G to A, at 417, C to A; at 534, T to C; at 741, C to T; and at 825, C to G. The three positive clones were sequenced, the first clone resulting in SEQ ID NO:1, the second clone resulting in SEQ ID NO:2 and the third clone resulting in SEQ ID NO:7. These isoforms all lack the initiation codon methionine.

EXAMPLE 2

Expression of Recombinant Multifunctional Protein Enzyme

A recombinant multifunctional protein was expressed in an *E.coli* as follows, using the BamHI and Xho I sites of a pET23c vector provided by Novagen (Abingdon, Oxford, U.K.). The pET23c vector includes a gene10 tag for facilitating purification of the expressed recombinant protein. Further, the pET vector places the recombinant multifunctional protein under the control of bacteriophage T7 transcription and translation signals. Once established in a non-expression host, *E. coli* MC 1061, the plasmid was then transferred to an expression host, *E. coli* BL21 (DE3) pLYS S having a chromosomal copy of the T7 polymerase gene under lacUV5 control. Expression was induced by the addition of 1 mM IPTG at an optical density of 0.5 at wavelength 600. The cells were harvested after 2 hours at an optical density of 1.0. The recombinant protein was insoluble in the lysate and after harvesting, it was washed and dissolved in 6 M urea. Refolding of the recombinant protein was carried out by 200-fold dilution using a buffer containing 100 mM tris HCl pH 9.5, 100 mM $CaCl_2$, 0.3 mM oxidized glutathione and 3 mM reduced glutathione, followed by stirring overnight at 4 C.

EXAMPLE 3

A fragment from the p62 clone that encodes amino acids 56 to 300 and the stop codon (see SEQ ID NOs: 1 an 4) was excised and inserted it into a pET-23c expression vector. Note that this clone excludes the cysteine required to form a disulfide link to a light chain. The encoded protein was expressed in *E. coli* strain BL21(DE3)pLysS, which yielded an insoluble material. The insoluble material was dissolved in 6 M urea, and re-folded by a 200-fold dilution into an aqueous solution buffered at pH 9.5, containing 0.1 mM CaCl and oxidized/reduced glutathione. The resulting solution was concentrated to recover the recombinant protein.

The recombinant protein was shown to cleave the model substrate succinyl-ala-ala-pro-phe-p-nitroanilide, thereby demonstrating its proteolytic activity. The proteolytic activity was inhibited by the protease inhibitor Eglin.

The nucleic acid sequences described herein, and consequently the protein sequences derived therefrom, have been carefully sequenced. However, those of ordinary skill will recognize that nucleic acid sequencing technology can be susceptable susceptible to some inadvertent error. Those of ordinary skill in the relevant arts are capable of validating or correcting these sequences based on the ample description herein of methods of isolating the nucleic acid sequences in question, and such modifications that are made readily available by the present disclosure are encompassed by the present invention. Furthermore, those sequences reported herein are believed to define functional biological macromolecules within the invention whether or not later clarifying studies identify sequencing errors.

The application describes a number of nucleic acid sequences, of which the more germane are summarized below.

| Short name | Nucleic Acid SEQ ID | Protein SEQ ID | Description |
|---|---|---|---|
| p62 | 1 | 4 | Nucleic acid codes an LLLALVAAASAAEWRW sequence through to the end of the reading frame (as indicated by two in-frame stop codons). |

-continued

| Short name | Nucleic Acid SEQ ID | Protein SEQ ID | Description |
|---|---|---|---|
| p31 | 2 | 5 | Nucleic acid codes a sequence that is extremely homologous to that being at AA117 of p62 through to the end of the reading frame. |
| — | 3 | 6 | Nucleic acid codes AA1-117 from p62, with the remainder corresponding to p31. |
| p5.1a | 7 | 8 | Nucleic acid codes a sequence that is extremely homologous to AA1-170 of p62, plus an additional 7-amino acid sequence fused to the N-terminus. |
| — | 9 | 10 | Nucleic acid codes AA1-123 from p5.1, with the remainder corresponding to p31. |
| p13 | 19 | 20 | Nucleic acid encodes a sequence that is extremely homologous to AA73-283 of p62. |
| p912 | 21 | 22 | Nucleic acid encodes a sequence that is extremely homologous to AA1-300 of p62, plus an additional 2-amino acid fused to the N-terminus. |
| p5.1b | 23 | 24 | Nucleic acid codes a sequence that is extremely homologous to AA1-170 of p62, plus an additional 7-amino acid sequence fused to the N-terminus. Comprises a consensus sequence derived from four PCR products. |

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow.

What is claimed:

1. An isolated nucleic acid comprising at least one of:
   (a) a nucleic acid encoding a polypeptide comprising a sequence which is AA64–300 of SEQ ID NO:4 or a sequence identical to AA64–300 of SEQ ID NO:4 except that it has one or more amino acid substitutions found in SEQ ID NOs: 5, 20, 22, or 24, or has glutamine, methionine, lysine or asparagine at amino acid residue 68 of SEQ ID NO:4; or (b) a polynucleotide which is fully complementary to the polynucleotide of (a).

2. A transformed cell comprising the nucleic acid of claim 1.

3. An expression vector comprising the nucleic acid of claim 1.

4. A polypeptide encoded by the nucleic acid of claim 1.

5. The polypeptide of claim 4, comprising at least one of the amino acid sequences selected from AA64–300 of SEQ ID NO:4, SEQ ID NO:5, SEQ ID NO:20, AA66–302 of SEQ ID NO:22 or AA72–178 of SEQ ID NO:24.

6. A method of preparing a proteinase comprising:
   (a) transforming a cell with an expression vector for expressing a nucleic acid encoding a polypeptide comprising a sequence which is AA64–300 of SEQ ID NO:4 or identical to AA64–300 of SEQ ID NO:4 except that it has one or more amino acid substitutions found in SEQ ID NOs: 5, 20, 22, or 24 or has glutamine, methionine, lysine or asparagine at amino acid residue 68 of SEQ ID NO:4;
   (b) growing the transformed cell in culture; and
   (c) isolating the protein.

* * * * *